United States Patent
Pathak et al.

(10) Patent No.: US 11,697,793 B2
(45) Date of Patent: Jul. 11, 2023

(54) COMPOSITIONS AND METHODS OF MAKING AND USING PROTEIN-FUNCTIONALIZED HYDROGELS

(71) Applicants: Amit Pathak, St. Louis, MO (US); Bapi Sarker, St. Louis, MO (US)

(72) Inventors: Amit Pathak, St. Louis, MO (US); Bapi Sarker, St. Louis, MO (US)

(73) Assignee: Washington University, St. Louis, MO (US)

( * ) Notice: Subject to any disclaimer, the term of this patent is extended or adjusted under 35 U.S.C. 154(b) by 854 days.

(21) Appl. No.: 16/598,676

(22) Filed: Oct. 10, 2019

(65) Prior Publication Data

US 2020/0115675 A1    Apr. 16, 2020

Related U.S. Application Data

(60) Provisional application No. 62/743,610, filed on Oct. 10, 2018.

(51) Int. Cl.
| | |
|---|---|
| C12N 5/00 | (2006.01) |
| C08F 220/58 | (2006.01) |
| C08F 220/56 | (2006.01) |
| C08F 222/38 | (2006.01) |
| G01N 33/48 | (2006.01) |
| G01N 33/50 | (2006.01) |
| C07C 233/31 | (2006.01) |
| G01N 33/483 | (2006.01) |

(52) U.S. Cl.
CPC .......... *C12N 5/0018* (2013.01); *C07C 233/31* (2013.01); *C08F 220/56* (2013.01); *C08F 220/58* (2013.01); *C08F 222/385* (2013.01); *G01N 33/4833* (2013.01); *G01N 33/5029* (2013.01); *C12N 2533/30* (2013.01); *C12N 2533/54* (2013.01); *C12N 2537/10* (2013.01)

(58) Field of Classification Search
CPC .............. C12N 5/0018; C12N 2533/30; C12N 2533/54; C12N 2537/10; C08F 220/56; C08F 220/58; C08F 222/385; G01N 33/4833; G01N 33/5029; C07C 233/31
USPC ...................................................... 525/326.4
See application file for complete search history.

(56) References Cited

U.S. PATENT DOCUMENTS

| | | | |
|---|---|---|---|
| 2006/0111517 A1* | 5/2006 | Feucht ............... | C12Q 1/002 525/329.4 |
| 2015/0104812 A1* | 4/2015 | Grevesse ............ | C08F 220/56 435/377 |

FOREIGN PATENT DOCUMENTS

CN    110950772 A  *  4/2020

OTHER PUBLICATIONS

Sarker et al. Direct Micropatterning of Extracellular Matrix Proteins on Functionalized Polyacrylamide Hydrogels Shows Geometric Regulation of Cell-Cell Junctions, ACS Biomaterials Science & Engineering (2018), 4(7), 2340-2349. (Year: 2018).*
Stephens-Altus et al. Development of bioactive photocrosslinkable fibrous hydrogels, Journal of Biomedical Materials Research, Part A (2011), 98A(2), 167-176. (Year: 2011).*
Aragona M, et al. (2013) A mechanical checkpoint controls multicellular growth through YAP/TAZ regulation by actin-processing factors. *Cell* 154(5):1047-1059.
Bae YH, et al. (2014) A FAK-Cas-Rac-Lamellipodin Signaling Module Transduces Extracellular Matrix Stiffness into Mechanosensitive Cell Cycling. *Science Signaling* 7(330):ra57.
Bredfeldt JS, et al. (2014) Computational segmentation of collagen fibers from second-harmonic generation images of breast cancer. (SPIE), p. 11.
Corey EJ & Suggs JW (1975) Pyridinium chlorochromate. An efficient reagent for oxidation of primary and secondary alcohols to carbonyl compounds. *Tetrahedron Letters* 16:2647-2650.
Dang TT, Prechtl AM, & Pearson GW (2011) Breast Cancer Subtype-Specific Interactions with the Microenvironment Dictate Mechanisms of Invasion. *Cancer Research* 71(21):6857.
Discher DE, Janmey P, & Wang Y-l (2005) Tissue Cells Feel and Respond to the Stiffness of Their Substrate. *Science* 310(5751):1139-1143.
Doyle AD, Carvajal N, Jin A, Matsumoto K, & Yamada KM (2015) Local 3D matrix microenvironment regulates cell migration through spatiotemporal dynamics of contractility-dependent adhesions. *Nature communications* 6:8720.
Dupont S, et al. (2011) Role of YAP/TAZ in mechanotransduction. *Nature* 474:179-183.
Ehrlich JS, Hansen MDH, & Nelson WJ (2002) Spatio-temporal regulation of Rac1 localization and lamellipodia dynamics during epithelial cell-cell adhesion. *Developmental cell* 3(2):259-270.
Elkhatib N, et al. (2017) Tubular clathrin/AP-2 lattices pinch collagen fibers to support 3D cell migration. *Science* 356(6343).
Elliott JT, Tona A, Woodward JT, Jones PL, & Plant AL (2003) Thin Films of Collagen Affect Smooth Muscle Cell Morphology. *Langmuir: the ACS journal of surfaces and colloids* 19(5):1506-1514.
Elosegui-Artola A, et al. (2017) Force Triggers YAP Nuclear Entry by Regulating Transport across Nuclear Pores. *Cell* 171(6):1397-1410 e1314.
Engler AJ, Sen S, Sweeney HL, & Discher DE (2006) Matrix Elasticity Directs Stem Cell Lineage Specification. *Cell* 126(4):677-689.
Fischer RS, Myers KA, Gardel ML, & Waterman CM (2012) Stiffness-controlled three-dimensional extracellular matrices for high-resolution imaging of cell behavior. *Nature protocols* 7(11):2056-2066.
Friedl P & Gilmour D (2009) Collective cell migration in morphogenesis, regeneration and cancer. *Nature reviews. Molecular cell biology* 10:445-457.
Gaggioli C, et al. (2007) Fibroblast-led collective invasion of carcinoma cells with differing roles for RhoGTPases in leading and following cells. *Nature cell biology* 9:1392.

(Continued)

*Primary Examiner* — Michael M. Bernshteyn

(57) ABSTRACT

Among the various aspects of the present disclosure is the provision of a hydrogel-based substrate comprising an aldehyde-containing component, such as N-ethanal acrylamide. The hydrogel component allows for functionalization of a hydrogel through conjugation of proteins (e.g., collagen) to the hydrogel in the absence of a post hoc crosslinking component.

7 Claims, 22 Drawing Sheets

(56) References Cited

OTHER PUBLICATIONS

Garcia S, et al. (2015) Physics of active jamming during collective cellular motion in a monolayer. *Proceedings of the National Academy of Sciences* 112(50):15314.
Gumbiner BM & Kim NG (2014) The Hippo-YAP signaling pathway and contact inhibition of growth. *Journal of cell science* 127(Pt 4):709-717.
Gurry T, Nerenberg PS, & Stultz CM (2010) The contribution of interchain salt bridges to triple-helical stability in collagen. *Biophysical journal* 98(11):2634-2643.
Han W, et al. (2016) Oriented collagen fibers direct tumor cell intravasation. *Proceedings of the National Academy of Sciences* 113(40):11208-11213.
Jean L, et al. (2013) Activation of Rac by Asef2 promotes myosin II-dependent contractility to inhibit cell migration on type I collagen. *Journal of cell science* 126(24):5585.
Lee JP, Kassianidou E, MacDonald JI, Francis MB, & Kumar S (2016) N-terminal Specific Conjugation of Extracellular Matrix Proteins to 2-Pyridinecarboxaldehyde Functionalized Polyacrylamide Hydrogels. *Biomaterials* 102:268-276.
Mack NA, Whalley HJ, Castillo-Lluva S, & Malliri A (2011) The diverse roles of Rac signaling in tumorigenesis. *Cell Cycle* 10(10):1571-1581.
Mackay JL & Kumar S (2013) Measuring the elastic properties of living cells with atomic force microscopy indentation. *Methods in molecular biology* (Clifton, N.J.) 931:313-329.
Mayor R & Etienne-Manneville S (2016) The front and rear of collective cell migration. *Nature Reviews Molecular Cell Biology* 17:97.
McDaniel DP, et al. (2007) The Stiffness of Collagen Fibrils Influences Vascular Smooth Muscle Cell Phenotype. *Biophysical journal* 92(5):1759-1769.
Mouw JK, Ou G, & Weaver VM (2014) Extracellular matrix assembly: a multiscale deconstruction. *Nature reviews. Molecular cell biology* 15(12):771-785.
Nasrollahi S & Pathak A (2016) Topographic confinement of epithelial clusters induces epithelial-to-mesenchymal transition in compliant matrices. *Scientific reports* 6:18831.
Nasrollahi S, et al. (2017) Past matrix stiffness primes epithelial cells and regulates their future collective migration through a mechanical memory. *Biomaterials* 146:146-155.
Ng MR, Besser A, Danuser G, & Brugge JS (2012) Substrate stiffness regulates cadherin-dependent collective migration through myosin-II contractility. *J Cell Biol* 199(3):545-563.
Pelham RJ & Wang Y-l (1997) Cell locomotion and focal adhesions are regulated by substrate flexibility. *Proceedings of the National Academy of Sciences*, USA 94(25):13661-13665 with 1998 correction attached (2 pages).

Persikov AV, Ramshaw JAM, Kirkpatrick A, & Brodsky B (2005) Electrostatic interactions involving lysine make major contributions to collagen triple-helix stability. *Biochemistry* 44(5):1414-1422.
Riching KM, et al. (2014) 3D collagen alignment limits protrusions to enhance breast cancer cell persistence. *Biophysical journal* 107(11):2546-2558.
Saha K, et al. (2008) Substrate Modulus Directs Neural Stem Cell Behavior. *Biophysical journal* 95:4426-4438.
Sarker B, et al. (2014) Fabrication of alginate-gelatin crosslinked hydrogel microcapsules and evaluation of the microstructure and physico-chemical properties. *Journal of Materials Chemistry B* 2:1470.
Sharma P, et al. (2017) Aligned fibers direct collective cell migration to engineer closing and nonclosing wound gaps. *Molecular Biology of the Cell* 28(19):2579-2588.
Tarle V, Ravasio A, Hakim V, & Gov NS (2015) Modeling the finger instability in an expanding cell monolayer. *Integrative Biology* 7(10):1218-1227.
Trappmann et al. (2012) Extracellular-matrix tethering regulates stem-cell fate. Nature Materials pp. 1-10 DOI: 10.1038/NMAT3339.
Ulrich Ta, De Juan Pardo EM, & Kumar S (2009) The mechanical rigidity of the extracellular matrix regulates the structure, motility, and proliferation of glioma cells. *Cancer Research* 69:4167-4174.
Wen et al. (2014) Interplay of Matrix Stiffness and Protein Tethering in Stem Cell Differentiation Nat Mater. 13(10): 979-987. doi:10.1038/nmat4051.
Wirtz D, Konstantopoulos K, & Searson PC (2011) The physics of cancer: the role of physical interactions and mechanical forces in metastasis. *Nature reviews. Cancer* 11(7):512-522.
Wolf K, et al. (2007) Multi-step pericellular proteolysis controls the transition from individual to collective cancer cell invasion. *Nature cell biology* 9:893-904.
Yamaguchi N, Mizutani T, Kawabata K, & Haga H (2015) Leader cells regulate collective cell migration via Rac activation in the downstream signaling of integrin beta1 and PI3K. *Scientific reports* 5:7656.
Yu X & Machesky LM (2012) Cells assemble invadopodia-like structures and invade into matrigel in a matrix metalloprotease dependent manner in the circular invasion assay. *PloS one* 7(2):e30605.
Zaman MH, et al. (2006) Migration of tumor cells in 3D matrices is governed by matrix stiffness along with cell-matrix adhesion and proteolysis. *Proceedings of the National Academy of Sciences of the United States of America* 103:10889-10894.
Zorn ML, Marel A-K, Segerer FJ, & Rädler JO (2015) Phenomenological approaches to collective behavior in epithelial cell migration. *Biochimica et Biophysica Acta (BBA)—Molecular Cell Research* 1853(11, Part B):3143-3152.

* cited by examiner

COMPOSITIONS AND METHODS OF MAKING AND USING PROTEIN-FUNCTIONALIZED HYDROGELS

CROSS-REFERENCE TO RELATED APPLICATIONS

This application claims priority from U.S. Provisional Application Ser. No. 62/743,610 filed on 10 Oct. 2018, which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

Not applicable.

FIELD OF THE INVENTION

The present disclosure generally relates to methods and compositions directed at functionalizing hydrogels.

SUMMARY OF THE INVENTION

Among the various aspects of the present disclosure is the provision of a substrate comprising an aldehyde containing acrylamide hydrogel component, such as N-ethanal acrylamide. The hydrogel component allows for functionalization of a polyacrylamide hydrogel through conjugation of proteins (e.g., collagen) to the hydrogel.

The present disclosure provides for compositions and methods for a protein-functionalizable polyacrylamide hydrogel. The functionalizable hydrogel can comprise acrylamide, bis-acrylamide, N-ethanal acrylamide, or a conjugated protein.

An aspect of the present disclosure provides for a substrate comprising an aldehyde-based polyacrylamide (PA) hydrogel comprising an aldehyde-containing acrylamide suitable for protein functionalization, wherein protein functionalization of the PA hydrogel enables protein fiber formation of a tunable protein fiber length.

In some embodiments, the aldehyde-containing acrylamide is an N-ethanal acrylamide (EA) monomer of formula I

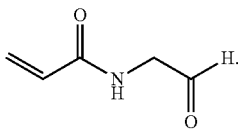

(I)

In some embodiments, the functionalized PA hydrogel further comprises an acrylamide co-polymer and a bis-acrylamide monomer crosslinker.

In some embodiments, the PA hydrogel comprises: (i) between about 1% and about 20% acrylamide by volume; (ii) between about 0.05% and about 5% bis-acrylamide by volume; or (iii) between about 0.5% and about 2% N-ethanal acrylamide by volume.

In some embodiments, the PA hydrogel has a Young's modulus or stiffness between about 0.1 kPa and about 200 kPa.

In some embodiments, an extracellular matrix (ECM) protein, optionally collagen, comprising an N-termini (ε-amino groups) region, is bound to an aldehyde group of the aldehyde-containing acrylamide.

In some embodiments, the substrate does not comprise an intermediate post hoc crosslinker, optionally, sulfosuccinimidyl 6-[4'-azido-2'-nitro-phenylamino] hexanoate (sulfo-SANPAH), or N-Hydroxysuccinimide (NHS)-ethyl (dimethylaminopropyl) carbodiimide (EDC) for use in protein functionalization.

In some embodiments, (i) the tunable protein fiber length average is between about 0.1 μm and 100 μm; or (ii) the substrate is a stiff substrate if a Young's moduli of the substrate is more than about 2 kPa or the substrate is a soft substrate if a Young's moduli of the substrate is less than about 2 kPa.

In some embodiments, the protein fiber length is tunable and independent of the substrate stiffness.

An aspect of the present disclosure provides for a method of preparing an aldehyde-functionalized polyacrylamide (PA) hydrogel, comprising: providing an acrylamide monomer and optionally an acrylamide crosslinker monomer; providing an aldehyde-containing acrylamide monomer, optionally, N-ethanal acrylamide; providing a polymerization initiator; combining the aldehyde-containing acrylamide and the polymerization initiator; or forming a PA hydrogel.

In some embodiments, the method is performed in the absence of a post-hoc cross-linker, optionally, NHS-ester-based crosslinkers, such as sulfo-SANPAH.

In some embodiments, the acrylamide monomer is acrylamide, the acrylamide crosslinker is bis-acrylamide, or the aldehyde-containing acrylamide is N-ethanal acrylamide.

In some embodiments, (i) the acrylamide monomer is between about 1% and about 20% acrylamide monomer by volume; (ii) the acrylamide crosslinker monomer is between about 0.05% and about 5% acrylamide crosslinker monomer by volume; or (iii) the aldehyde-containing acrylamide monomer is between about 0.5% and about 2% N-ethanal acrylamide monomer by volume.

In some embodiments, the PA hydrogel has a Young's modulus or stiffness between about 0.1 kPa and about 200 kPa.

In some embodiments, the method further comprises: providing a protein, optionally, collagen; or functionalizing the PA hydrogel with the protein, wherein the protein is capable of forming tunable protein fiber length.

In some embodiments, the method is performed in the absence of a post-hoc crosslinker, capable of protein binding, optionally, NHS-ester-based crosslinkers, such as sulfo-SANPAH).

In some embodiments, the method further comprises incubating the PA hydrogel and the protein for an amount of time and at an incubation temperature sufficient to form a protein-functionalized PA hydrogel having a tunable protein fiber length.

In some embodiments, the time sufficient to form long protein fibers is between about 30 minutes and below about 5 hours or the incubation temperature is between about 4° C. and about 37° C.

In some embodiments, the method comprises culturing cells on the protein-functionalized PA hydrogel, wherein long protein fibers result in formation of multi-cell streams of faster cell migration, enhanced cell elongation, Yes-associated protein (YAP) activity, or actin alignment when compared to cell migration on short fibers.

In some embodiments, the PA hydrogel is protein-functionalized through conjugation of the protein to the aldehyde-containing acrylamide, optionally, N-ethanal acrylamide.

In some embodiments, the protein is an extracellular matrix (ECM) protein, collagen, collagen fibers, elastin, fibronectin, or laminin.

In some embodiments, (i) the tunable protein fiber length average is between about 0.1 μm and 100 μm; or (ii) the PA hydrogel is a stiff substrate if a Young's moduli of the substrate is more than about 2 kPa or the substrate is a soft substrate if a Young's moduli of a substrate is less than about 2 kPa.

In some embodiments, the protein fiber length is tunable and independent of the substrate stiffness.

In some embodiments, a long collagen fiber length and a soft hydrogel result in more robust multi-cellular collective cell streaming when compared to a more rigid substrate.

Another aspect of the present disclosure provides for a cell culture system, comprising seeding cells onto a surface of a substrate comprising a protein-functionalized PA hydrogel of claim 5, wherein the cells are an immortalized cell line, a primary cell line, a cancer cell line, a homologous or heterologous cell population able to replicate in cell culture conditions, MCF10A cells, an epithelial cell line, immune cells, T cells, human cells, mouse cells, or mammalian cells.

Yet another aspect of the present disclosure provides for a method of performing mechanobiology studies of cell migration using a cell culture system, comprising: imaging or analyzing the cells through microscopy; or measuring or analyzing cellular extensions, streams, blebs, extension area, extension velocity, or protein expression.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1A:
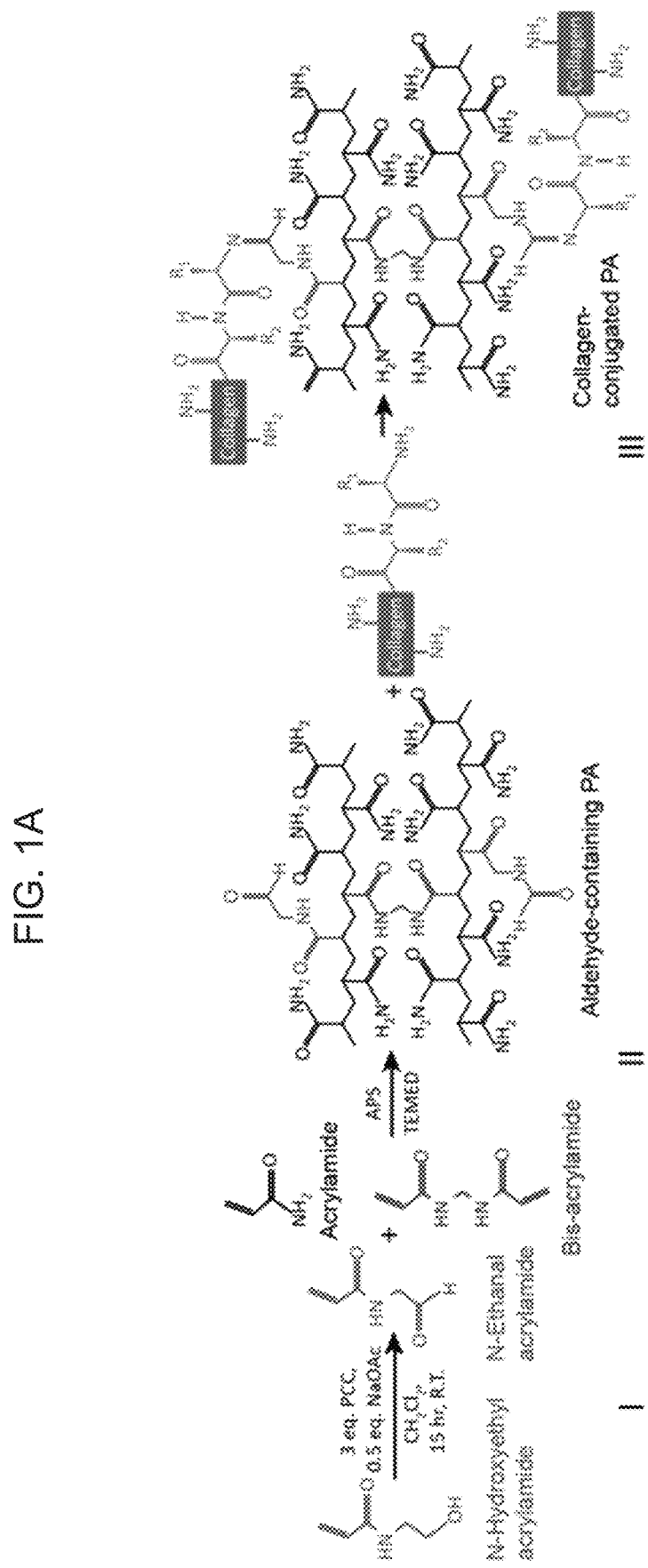
FIG. 1A-FIG. 1E is a series of schemes, graphs, and images showing chemical modification of polyacrylamide (PA) facilitates collagen tethering with controllable fibrous conformation. (A) A reaction schematic shows the steps associated with the chemical medication of PA and conjugation of collagen to the modified PA. First step shows oxidation of N-hydroxyethyl acrylamide (HEA), where aldehyde-containing N-ethanal acrylamide (EA) is formed. In the second step, EA is copolymerized with acrylamide and bis-acrylamide to synthesize aldehyde-containing PA. The third step shows the conjugation of collagen to the PA through formation of Schiff's base bond (carbon-nitrogen double bond) between N-termini (ε-amino groups) of collagen and aldehyde groups of the modified PA. (B) Young's moduli of modified PA gels with varying acrylamide and bis-acrylamide ratio, where EA was added to the PA gel precursor mixtures at a volume ratio of 1:75 (EA:acrylamide). (C) Confocal microscopy images of fluorescently labelled collagen I on soft and stiff PA gels. Collagen coating was performed at different temperatures for certain times. Scale bar=100 μm. (D) Length of collagen fibers on different substrates. Asterisks denote significant difference (p<0.05) between long and short fibers within the same stiffness. (E) SEM images of MCF10A cells in the leading edge of migrating epithelial monolayer, showing long collagen fibers (shown with arrow, top) guide cell in certain direction on Soft PA, long fiber substrate and more flattened leading edge cells are grown on small collagen fibers (shown with arrow, bottom) on Soft PA, short fiber gel. Scale bar=6 μm.

The present disclosure is based, at least in part, on the discovery that a precursor additive increases the performance to yield a completely functionalized hydrogel without any need for a post-hoc crosslinker. As shown herein, the present disclosure provides for aldehyde-based functionalization of polyacrylamide hydrogels.

The present disclosure provides for a polyacrylamide (PA) precursor additive compound, N-ethanal acrylamide, and methods for synthesizing PA hydrogels that are pre-functionalized for protein coating, such that the PA hydrogels do not require a post-hoc crosslinker to facilitate subsequent protein coating or conjugation. More specifically, collagen fiber formation is promoted when the aldehyde-based functionalized PA hydrogels are coated or functionalized with collagen proteins. In the present disclosure, collagen fiber length is tunable and independent of the PA hydrogel (i.e., substrate) stiffness.

In cell mechanobiology studies, polyacrylamide (PA) is a very popular hydrogel system. To attach proteins to the PA gels (for cell culture), crosslinkers, such as Sulfo-SANPAH, have been previously used. However, this method yields an unreliable protein coating and is prone to errors due to stringent requirements. Moreover, such conventional methods do not allow the coating of fibrous proteins, such as collagen-I, of varying fiber length. The disclosed PA system is pre-functionalized for protein coating with much more robust coating and varying fiber length. It is also easier and cheaper than existing technologies.

As described herein, a compound N-ethanal Acrylamide (which can also be referred to as NEAcry or NEtA) has been developed that can be added to any standard PA precursor solution to yield a completely functionalized hydrogel without any need for a post-hoc crosslinker.

As described herein, this compound can be used with hydrogels of varying stiffness and extracellular matrix (ECM) protein structures (see e.g., Example 1).

The disclosed aldehyde containing compound can be used for functionalization of hydrogels, which are widely used for cell culture applications. In immunotherapy, it is understood that soft hydrogels might be better for expanding T cells than standard tissue culture plastic. The presently disclosed compound can dramatically enhance the reliability of hydrogel functionalization, even on stiff surfaces.

Aldehyde-Containing Component

As described herein, an aldehyde-containing component can be used to provide for the protein functionalization of polyacrylamide hydrogels. For example, an aldehyde containing compound can be an acrylamide (e.g., N-ethanal acrylamide). As described herein, N-ethanal acrylamide is used as a precursor additive for the functionalization of PA hydrogels. N-ethanal acrylamide can also be referred to as N-(2-oxoethyl)acrylamide, N-acryloylamino-acetaldehyde, NEAcry, or NEtA. N-ethanal acrylamide is a chemical compound with the chemical formula $C_5H_7NO_2$, as shown in formula I:

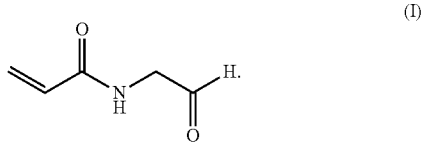

N-ethanal acrylamide can be synthesized from N-hydroxyethyl acrylamide. N-hydroxyethyl acrylamide (HEA) can be oxidized using pyridinium chlorochromate (PCC) to generate primary aldehyde groups in HEA molecules, as shown in scheme I:

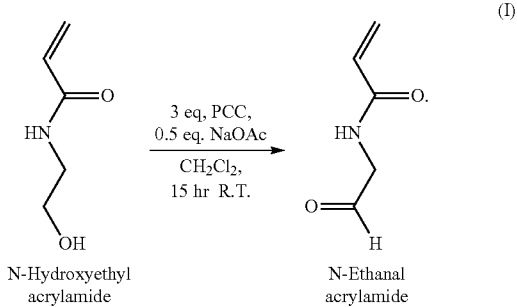

As another example, any acrylamide containing an aldehyde unit or monomer can be used to provide the PA with the ability to functionalize a protein.

Additional acrylamide components, such as bis-acrylamide and acrylamide monomers can also be used as copolymerization components. As described herein, bis-acrylamide can be used as a co-polymer cross-linker (see e.g., FIG. 1A).

Functionalized Hydrogel

As described herein, any hydrogel suitable for use in cell culture can be used. Furthermore, any hydrogel suitable for conjugation to proteins (e.g., ECM proteins, such as collagen) can be used. In particular, polyacrylamide hydrogels are suitable for use in protein conjugation.

Methods of making and choosing appropriate hydrogel systems are well known; see e.g. Ahmed 2015 J Adv Res. 6(2) 105-121; Calo 2015 Eur Poly J. 65 252-267. Except as otherwise noted herein, therefore, the process of the present disclosure can be carried out in accordance with such processes.

Compositions and methods as described herein provide for the use of polyacrylamide (PA) hydrogels. Components of PA hydrogels can comprise acrylamide, N,N'-methylenebisacrylamide (bis-acrylamide), and N-ethanal acrylamide monomers. As described herein, aldehyde-containing acrylamides are particularly suitable for the protein-functionalization of the PA gels.

In some embodiments, a co-polymer such as an acrylamide can comprise about 1% to about 50% of the hydrogel by volume. Preferably, the co-polymer (e.g., acrylamide) can comprise about 4% to 15% of the hydrogel by volume. For example, the co-polymer (e.g., acrylamide) can comprise about 1%; about 2%; about 3%; about 4%; about 5%; about 6%; about 7%; about 8%; about 9%; about 10%; about 11%; about 12%; about 13%; about 14%; about 15%; about 16%; about 17%; about 18%; about 19%; about 20%; about 21%; about 22%; about 23%; about 24%; about 25%; about 26%; about 27%; about 28%; about 29%; about 30%; about 31%; about 32%; about 33%; about 34%; about 35%; about 36%; about 37%; about 38%; about 39%; about 40%; about 41%; about 42%; about 43%; about 44%; about 45%; about 46%; about 47%; about 48%; about 49%; or about 50% of the hydrogel by volume.

In some embodiments, a co-polymer crosslinker, such as bis-acrylamide can comprise between about 0.1% and about 5% of the hydrogel by volume. Preferably, the co-polymer or crosslinker can comprise between about 0.2% and about 1.2% of the hydrogel by volume. For example, the co-polymer or crosslinker can comprise about 0.1%; 0.2%; 0.3%; 0.4%; 0.5%; 0.6%; 0.7%; 0.8%; 0.9%; 1%; 1.1%; 1.2%; 1.3%; 1.4%; 1.5%; 1.6%; 1.7%; 1.8%; 1.9%; 2%; 2.1%; 2.2%; 2.3%; 2.4%; 2.5%; 2.6%; 2.7%; 2.8%; 2.9%; 3%; 3.1%; 3.2%; 3.3%; 3.4%; 3.5%; 3.6%; 3.7%; 3.8%; 3.9%; 4%; 4.1%; 4.2%; 4.3%; 4.4%; 4.5%; 4.6%; 4.7%; 4.8%; 4.9%; or 5% of the hydrogel by volume.

In some embodiments, an aldehyde-containing co-polymer or acrylamide monomer, such as N-ethanal acrylamide, can be between about 0.1% and about 10% of the hydrogel by volume. Preferably, the aldehyde-containing polymer or acrylamide can be 1.33% (1:75) of the hydrogel by volume. For example, the aldehyde-containing polymer or acrylamide can be about 0.1%; 0.2%; 0.3%; 0.4%; 0.5%; 0.6%; 0.7%; 0.8%; 0.9%; 1%; 1.1%; 1.2%; 1.3%; 1.4%; 1.5%; 1.6%; 1.7%; 1.8%; 1.9%; 2%; 2.1%; 2.2%; 2.3%; 2.4%; 2.5%; 2.6%; 2.7%; 2.8%; 2.9%; 3%; 3.1%; 3.2%; 3.3%; 3.4%; 3.5%; 3.6%; 3.7%; 3.8%; 3.9%; 4%; 4.1%; 4.2%; 4.3%; 4.4%; 4.5%; 4.6%; 4.7%; 4.8%; 4.9%; 5%; 5.1%; 5.2%; 5.3%; 5.4%; 5.5%; 5.6%; 5.7%; 5.8%; 5.9%; 6%; 6.1%; 6.2%; 6.3%; 6.4%; 6.5%; 6.6%; 6.7%; 6.8%; 6.9%; 7%; 7.1%; 7.2%; 7.3%; 7.4%; 7.5%; 7.6%; 7.7%; 7.8%; 7.9%; 8%; 8.1%; 8.2%; 8.3%; 8.4%; 8.5%; 8.6%; 8.7%; 8.8%; 8.9%; 9%; 9.1%; 9.2%; 9.3%; 9.4%; 9.5%; 9.6%; 9.7%; 9.8%; 9.9%; or 10% by volume.

In some embodiments, the components of the hydrogel can be varied in order to vary the hydrogel stiffness. For example, the hydrogel stiffness can be varied from approximately 0.1 kilopascals (kPa) to approximately 200 kPa. Preferably, the hydrogel stiffness can be between about 0.1 kPa and about 100 kPa. For example, the hydrogel stiffness can be about 0.1 kPa; 0.2 kPa; 0.3 kPa; 0.4 kPa; 0.5 kPa; 0.6 kPa; 0.7 kPa; 0.8 kPa; 0.9 kPa; 1 kPa; 1.5 kPa; 2 kPa; 2.5 kPa; 3 kPa; 3.5 kPa; 4 kPa; 4.5 kPa; 5 kPa; 5.5 kPa; 6 kPa; 6.5 kPa; 7 kPa; 7.5 kPa; 8 kPa; 8.5 kPa; 9 kPa; 9.5 kPa; 10 kPa; 10.5 kPa; 11 kPa; 11.5 kPa; 12 kPa; 12.5 kPa; 13 kPa; 13.5 kPa; 14 kPa; 14.5 kPa; 15 kPa; 15.5 kPa; 16 kPa; 16.5 kPa; 17 kPa; 17.5 kPa; 18 kPa; 18.5 kPa; 19 kPa; 19.5 kPa; 20 kPa; 20.5 kPa; 21 kPa; 21.5 kPa; 22 kPa; 22.5 kPa; 23 kPa; 23.5 kPa; 24 kPa; 24.5 kPa; 25 kPa; 25.5 kPa; 26 kPa; 26.5 kPa; 27 kPa; 27.5 kPa; 28 kPa; 28.5 kPa; 29 kPa; 29.5 kPa; 30 kPa; 30.5 kPa; 31 kPa; 31.5 kPa; 32 kPa; 32.5 kPa; 33 kPa; 33.5 kPa; 34 kPa; 34.5 kPa; 35 kPa; 35.5 kPa; 36 kPa; 36.5 kPa; 37 kPa; 37.5 kPa; 38 kPa; 38.5 kPa; 39 kPa; 39.5 kPa; 40 kPa; 40.5 kPa; 41 kPa; 41.5 kPa; 42 kPa; 42.5 kPa; 43 kPa; 43.5 kPa; 44 kPa; 44.5 kPa; 45 kPa; 45.5 kPa; 46 kPa; 46.5 kPa; 47 kPa; 47.5 kPa; 48 kPa; 48.5 kPa; 49 kPa; 49.5 kPa; 50 kPa; 50.5 kPa; 51 kPa; 51.5 kPa; 52 kPa; 52.5 kPa; 53 kPa; 53.5 kPa; 54 kPa; 54.5 kPa; 55 kPa; 55.5 kPa; 56 kPa; 56.5 kPa; 57 kPa; 57.5 kPa; 58 kPa; 58.5 kPa; 59 kPa; 59.5 kPa; 60 kPa; 60.5 kPa; 61 kPa; 61.5 kPa; 62 kPa; 62.5 kPa; 63 kPa; 63.5 kPa; 64 kPa; 64.5 kPa; 65 kPa; 65.5 kPa; 66 kPa; 66.5 kPa; 67 kPa; 67.5 kPa; 68 kPa; 68.5 kPa; 69 kPa; 69.5 kPa; 70 kPa; 70.5 kPa; 71 kPa; 71.5 kPa; 72 kPa; 72.5 kPa; 73 kPa; 73.5 kPa; 74 kPa; 74.5 kPa; 75 kPa; 75.5 kPa; 76 kPa; 76.5 kPa; 77 kPa; 77.5 kPa; 78 kPa; 78.5 kPa; 79 kPa; 79.5 kPa; 80 kPa; 80.5 kPa; 81 kPa; 81.5 kPa; 82 kPa; 82.5 kPa; 83 kPa; 83.5 kPa; 84 kPa; 84.5 kPa; 85 kPa; 85.5 kPa; 86 kPa; 86.5 kPa; 87 kPa; 87.5 kPa; 88 kPa; 88.5 kPa; 89 kPa; 89.5 kPa; 90 kPa; 90.5 kPa; 91 kPa; 91.5 kPa; 92 kPa; 92.5 kPa; 93 kPa; 93.5 kPa; 94 kPa; 94.5 kPa; 95 kPa; 95.5 kPa; 96 kPa; 96.5 kPa; 97 kPa; 97.5 kPa; 98 kPa; 98.5 kPa; 99 kPa; 99.5 kPa; 100 kPa; 101 kPa; 102 kPa; 103 kPa, 104 kPa, 105 kPa, 106 kPa, 107 kPa, 108 kPa, 109 kPa, 110 kPa, 111 kPa; 112 kPa; 113 kPa; 114 kPa; 115 kPa; 116 kPa; 117 kPa; 118 kPa; 119 kPa; 120 kPa; 121 kPa; 122 kPa; 123 kPa; 124 kPa; 125 kPa; 126 kPa; 127 kPa; 128 kPa; 129 kPa; 130 kPa; 131 kPa; 132 kPa; 133 kPa; 134 kPa; 135 kPa; 136 kPa; 137 kPa; 138 kPa; 139 kPa; 140 kPa; 141 kPa; 142 kPa; 143 kPa; 144 kPa; 145 kPa; 146 kPa; 147 kPa; 148 kPa; 149 kPa; 150 kPa; 151 kPa; 152 kPa; 153 kPa; 154 kPa; 155 kPa; 156 kPa; 157 kPa; 158 kPa; 159 kPa; 160 kPa; 161 kPa; 162 kPa; 163 kPa; 164 kPa; 165 kPa; 166 kPa; 167 kPa; 168 kPa; 169 kPa; 170 kPa; 171 kPa; 172 kPa; 173 kPa; 174 kPa; 175 kPa; 176 kPa; 177 kPa; 178 kPa; 179 kPa; 180 kPa; 181 kPa; 182 kPa; 183 kPa; 184 kPa; 185 kPa; 186 kPa; 187 kPa; 188 kPa; 189 kPa; 190 kPa; 191 kPa; 192 kPa; 193 kPa; 194 kPa; 195 kPa; 196 kPa; 197 kPa; 198 kPa; 199 kPa; or 200 kPa.

In some embodiments, the temperature at which the hydrogel incubates can be varied to vary the hydrogel stiffness and ECM fiber length. Preferably, the incubation temperature can be between about 4° C. and about 37° C. For example, the temperature at which the hydrogel incubates can be about 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C.; 39° C.; 40° C.; 41° C.; 42° C.; 43° C.; 44° C.; 45° C.; 46° C.; 47° C.; 48° C.; 49° C.; or 50° C.

In some embodiments, the time at which the hydrogel incubates hydrogel can be varied to vary the hydrogel stiffness and ECM fiber length. For example, the time at which the hydrogel incubates can be at least about 1 minute; at least about 2 minutes; at least about 3 minutes; at least about 4 minutes; at least about 5 minutes; at least about 6 minutes; at least about 7 minutes; at least about 8 minutes; at least about 9 minutes; at least about 10 minutes; at least about 11 minutes; at least about 12 minutes; at least about 13 minutes; at least about 14 minutes; at least about 15 minutes; at least about 16 minutes; at least about 17 minutes; at least about 18 minutes; at least about 19 minutes; at least about 20 minutes; at least about 21 minutes; at least about 22 minutes; at least about 23 minutes; at least about 24 minutes; at least about 25 minutes; at least about 26 minutes; at least about 27 minutes; at least about 28; at least about 29 minutes; at least about 30 minutes; at least about 31 minutes; at least about 32 minutes; at least about 33 minutes; at least about 34 minutes; at least about 35 minutes; at least about 36 minutes; at least about 37 minutes; at least about 38 minutes; at least about 39 minutes; at least about 40 minutes; at least about 41 minutes; at least about 42 minutes; at least about 43 minutes; at least about 44 minutes; at least about 45 minutes; at least about 46 minutes; at least about 47 minutes; at least about 48 minutes; at least about 49 minutes; at least about 50 minutes; at least about 51 minutes; at least about 52 minutes; at least about 53 minutes; at least about 54 minutes; at least about 55 minutes; at least about 56 minutes; at least about 57 minutes; at least about 58 minutes; at least about 59 minutes; about 2 hours; about 3 hours; about 4 hours; about 5 hours; about 6 hours; about 7 hours; about 8 hours; about 9 hours; about 10 hours; about 11 hours; about 12 hours; about 13 hours; about 14 hours; about 15 hours; about 16 hours; about 17 hours; about 18 hours; about 19 hours; about 20 hours; about 21 hours; about 22 hours; about 23 hours; about 24 hours; about 25 hours; about 26 hours; about 27 hours; about 28 hours; about 29 hours; about 30 hours; about 31 hours; about 32 hours; about 33 hours; about 34 hours; about 35 hours; about 36 hours; about 37 hours; about 38 hours; about 39 hours; about 40 hours; about 41 hours; about 42 hours; about 43 hours; about 44 hours; about 45 hours; about 46 hours; about 47 hours; or about 48 hours.

Chemically modified PA gels with desired stiffness can be fabricated on any material, such as glass (e.g., coverslip), plastic, or a cell culture vessel. For example, PA precursor solutions can be prepared by mixing varying amounts of acrylamide, bis-acrylamide, and N-ethanal acrylamide. To initiate polymerization, ammonium persulfate (APS) and tetramethylethylenediamine (TEMED, Sigma) can be added to the precursor mixtures, as shown in scheme II:

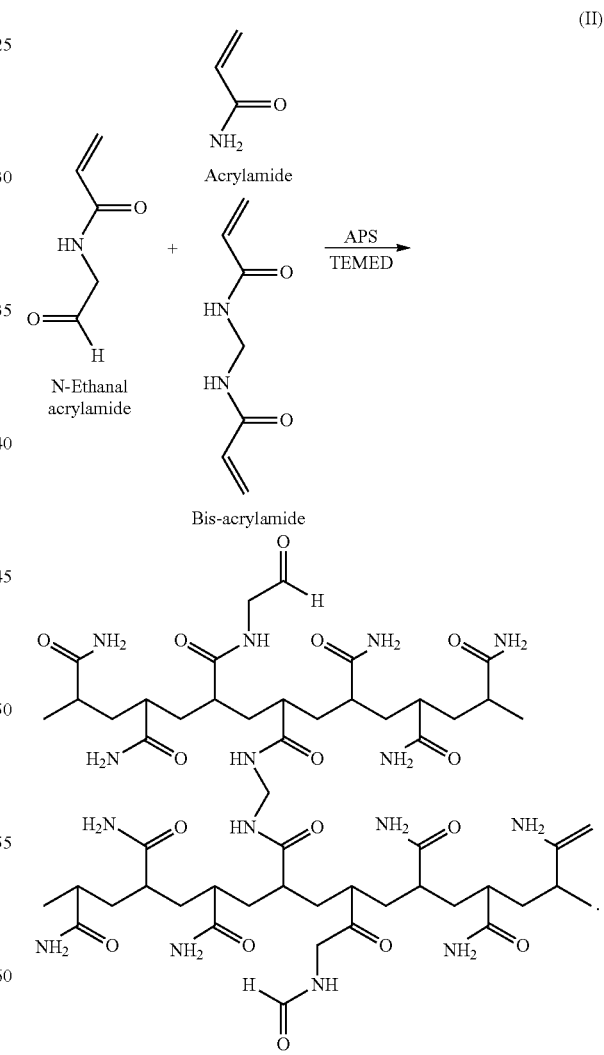

As described herein, aldehyde-containing hydrogels (e.g., PA hydrogel with N-ethanal acrylamide precursor additive) can be functionalized with protein, without the need for post-hoc crosslinkers. For example, the hydrogel can be functionalized with an extracellular matrix protein, such as collagen.

For example, a protein, such as an ECM protein (e.g., collagen) can be added to the aldehyde-containing hydrogel. The protein fibers can be a specific length. For example, the fibers can be between about 1 micron (μm) and about 100 μm on average. Collagen fiber length can thus be tunable, independent of the hydrogel stiffness. For example, the average protein fibers can be about 1 μm; 2 μm; 3 μm, 4 μm, 5 μm, 6 μm; 7 μm, 8 μm; 9 μm, 10 μm; 11%; about 12 μm; 13 μm; 14 μm; 15 μm; 16 μm; 17 μm; 18 μm; 19 μm; 20 μm; 21 μm; 22 μm; 23 μm; 24 μm; 25 μm; 26 μm; 27 μm; 28 μm; 29 μm; 30 μm; 31 μm; 32 μm; 33 μm; 34 μm; 35 μm; 36 μm; 37 μm; 38 μm; 39 μm; 40 μm; 41 μm; 42 μm; 43 μm; 44 μm; 45 μm; 46 μm; 47 μm; 48 μm; 49 μm; 50 μm; 51 μm; 52 μm; 53 μm; 54 μm; 55 μm; 56 μm; 57 μm; 58 μm; 59 μm; 60 μm; 61 μm; 62 μm; 63 μm; 64 μm; 65 μm; 66 μm; 67 μm; 68 μm; 69 μm; 70 μm; 71 μm; 72 μm; 73 μm; 74 μm; 75 μm; 76 μm; 77 μm; 78 μm; 79 μm; 80 μm; 81 μm; 82 μm; 83 μm; 84 μm; 85 μm; 86 μm; 87 μm; 88 μm; 89 μm; 90 μm; 91 μm; 92 μm; 93 μm; 94 μm; 95 μm; 96 μm; 97 μm; 98 μm; 99 μm; or 100 μm.

As another example, collagen can be added onto the PA surface and incubated for a length of time and temperature suitable for desired stiffness. For example, type I collagen can be incubated either overnight at 4° C. or 30 min at 37° C. Conjugation of collagen to the PA occurs through formation of Schiff's base bond (carbon-nitrogen double bond) between N-termini (ε-amino groups) of a protein (e.g., collagen) and aldehyde groups of the modified PA. For example, functionalization of the PA with collagen is shown in scheme III of FIG. 1A. $R_1$ and $R_2$ can be any suitable group known in the art.

Extracellular Matrix (ECM) Proteins

The hydrogels as described herein can be functionalized with proteins. For example, extracellular matrix (ECM) proteins can be used. As an example, the ECM protein, collagen, can be conjugated to the PA gel.

The collagen protein conjugated to the PA gel can be fibrillar (Type I, II, III, V, XI), non-fibrillar, FACIT (Fibril Associated Collagens with Interrupted Triple Helices) (Type IX, XII, XIV, XIX, XXI), short chain (Type VIII, X), basement membrane (Type IV), multiplexin (Multiple Triple Helix domains with Interruptions) (Type XV, XVIII), MACIT (Membrane Associated Collagens with Interrupted Triple Helices) (Type XIII, XVII), or other types including type VI and VII. The most common types of collagen include type I: skin, tendon, vasculature, organs, bone (main component of the organic part of bone); type II: cartilage (main collagenous component of cartilage); type III: reticulate (main component of reticular fibers), commonly found alongside type I; type IV: forms basal lamina, the epithelium-secreted layer of the basement membrane; and type V: cell surfaces, hair, and placenta.

Other ECM proteins that can be conjugated to the disclosed hydrogels can be elastin, fibronectin, or laminin.

Cell Culture Systems

The disclosed functionalized hydrogels can be used for cell culture applications. For example, semi-confluent or confluent cell monolayers can be formed on the surface of the disclosed protein-functionalized hydrogel. As another example, a small cell colony can be formed by placing a tiny droplet of cells onto the surface of the gel.

Any immortalized cell line, primary cell line, cancer cell line, or homologous or heterologous cell population able to replicate in cell culture conditions can be used for this cell culture system. For example, MCF10A cells or another epithelial cell line can be used. As another example, immune cells can be used, as in immunotherapy it is understood that soft hydrogels might be better for expanding T cells than standard tissue culture plastic. As another example, human, mice, or other mammalian cells can be used.

Furthermore, the disclosed protein-functionalized hydrogels can be used for mechanobiology studies of cell migration. For example, cells plated on the hydrogel can be imaged or analyzed through microscopy, including but not limited to time-lapse microscopy, live-cell imaging, phase contrast imaging, immunofluorescent confocal microscopy, or scanning electron microscopy.

Mechanobiology studies can include measurements or analyses of cellular extensions, streams, blebs, extension area, or extension velocity. Cells or cellular extension can also be analyzed for protein expression (e.g., F-actin, vimentin).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Increasing Collagen Fiber Length Enables Collective Cell Streaming on Aldehyde-Functionalized Compliant Hydrogels The following example describes the use of aldehyde-functionalized hydrogels to conjugate collagen proteins and promote long collagen fiber growth without post-hoc cross-linkers. It was shown that narrow multi-cellular streams of enhanced mechanoactivation emanate from the cell sheets on soft gels coated with long collagen fibers.

Epithelial cells migrate as sheets on 2D substrates and in narrow streams along collagen-I fibers in 3D. It remains unclear whether these distinct modes of collective cell migration—streams versus sheets—occur due to the differences in the matrix dimensionality or the collagen fiber architecture in tissue-like soft microenvironments. To address this question, a novel pre-functionalized polyacrylamide (fPA) hydrogel system was introduced by inserting aldehyde-based active sites for protein attachment within the polymeric PA network, which enables collagen-I coating of tunable fiber length. It is reported here that epithelial monolayers cultured on soft fPA gels with long fibers (LF) emanate multi-cell streams of faster and more correlated migration, along with enhanced cell elongation yes-associated protein (YAP) activity and actin alignment, compared to the sheet-like migration on short fibers (SF). Surprisingly, on stiff-LF substrates, cellular streaming was less persistent due to a loss of cell-cell adhesions and reduced correlation in cell velocities behind any incipient streams. Thus, the impact of fiber length on the collective migration phenotype was more pronounced on softer extracellular matrix (ECM). After Rac inhibition, the reduced elongation and correlated migration of cells rendered them unable to exploit the long fibers to undergo collective cell streaming. These findings indicate that the formation of invasion-like multicellular streams with enhanced cellular mechanoactivation requires a delicate balance of cell elongation, cell-cell adhesions, and correlated collective migration, all of which depend on matrix stiffness and fiber length. Beyond this work, this novel fPA gel system will improve protein attachment, without the post-hoc cross-linkers, for wide-ranging cell mechanobiology studies.

Through 3D fibrous matrices, grouped cells move in narrow streams, which is different from the sheet-like migration observed on flat surfaces. It was tested whether collective cell streaming could occur on 2D soft substrates with long collagen-I fibers. Through a new pre-functionalized hydrogel system, it is demonstrated here that narrow multicellular streams of enhanced mechanoactivation emanate from the cell sheets on soft gels coated with long collagen fibers. However, both stiff matrices and shorter fibers disrupt the ideal balance of cell elongation, cell-cell adhesions and cellular mechanoactivation required for sustained collective cell streaming. The present disclosure provides for an improved hydrogel design for cell mechanobiology studies and shows that fiber architecture can alter the modes of collective cell migration independently of matrix stiffness and dimensionality.

Introduction

Collective cell migration is a fundamental biological process in tissue and organ morphogenesis, wound healing, angiogenesis, and cancer progression. Epithelial cells that preferably migrate collectively have been observed form sheet-like structures on 2D substrates. It is well established that substrate stiffness regulates cadherin-based collective cell migration in 2D, which is mediated through myosin-II contractility. However, in 3D extracellular matrix (ECM), the common mode of collective migration is in the form of narrow multi-cellular streams guided by collagen fibers, which is quite different from the sheet-like migration in 2D. To accommodate the spatial constraints of the 3D microenvironment that surrounds the multi-cellular streams, leader cells create migratory tracks through protease- and force-mediated matrix remodeling of least mechanical resistance. However, the protease- and force-mediated matrix remodeling is caused by mesenchymal cells or the cells with upregulated mesenchymal and mechanoactivation markers. The conventional 2D in vitro platforms for cell migration studies do not allow the formation of such multi-cellular streams due to the lack of ECM fibers that are found in 3D ECMs. Although cell streaming has been observed on 2D substrate with artificially aligned synthetic fibers, this substrate does not mimic the physiological environment due to the absence of ECM proteins. It remains unclear whether multi-cellular streaming can occur on non-aligned long collagen fibers on 2D substrates. Importantly, it remains unknown whether substrate stiffness plays a role in regulating the mode of collective cell migration on substrates with long collagen fibers because traditionally stiff ECM is considered to enable aggressive invasion through enhanced epithelial-mesenchymal transition (EMT) and mechanoactivation.

To mimic the native ECM condition in 2D and investigate the effect of ECM stiffness on collective cell migration, it is necessary to make fibrous collagen structure on polyacrylamide (PA) hydrogel, which has been a popular material system for cell culture in seminal mechanobiology studies of the past decade. The PA's popularity is mainly attributed to its tunability between ~0.1-100 kPa, mimicking the stiffness range of soft tissues in both healthy and disease conditions. Moreover, in order to understand the role of collagen fiber dimension on collective cell migration in 2D, the fibrous structure of collagen should be tunable independent of PA stiffness. On conventional PA gels functionalized with the NHS-ester-based crosslinkers (e.g., sulfo-SANPAH), it has remained difficult to achieve native ECM-like fibrous structure of collagen on 2D substrates. Naturally, collagen has the ability to self-assemble into a hierarchical structure and several studies reported that monomeric collagen deposited onto rigid substrates and self-assembled into fibrils and fibers. However, sulfo-SANPAH-treated PA gel could trigger non-specific protein conjugation, resulting in a blockade of the lysine residues that are required for triple helix formation. Previous studies have functionalized polyacrylamide hydrogel systems with 2-pyridinecarboxaldehyde to coat collagen fibers. As shown herein, the tunability of collagen fiber length independent of PA stiffness is explored. In this study, a methodology of deposition of collagen fiber of tunable dimension on aldehyde-functionalized PA gel in introduced. The collagen incubation temperature was varied to tune fiber length within the novel fPA gel system that not only promotes fiber formation but also allows the tuning of fiber structure independent of the substrate stiffness. Though it is known that collagen fibers support contact guidance and control morphology and migration of single cells in 3D ECM, little is known about how the collagen fibers regulate collective cell migration. Because it is extremely difficult to investigate the role of collagen fibers and the effect of ECM stiffness on the collective cell migration in 3D matrix, the 2D material system of independently tunable stiffness and fiber length described here presents a new material paradigm for deconstructing the influences of these two critical matrix parameters on varying modes of collective cell migration. The experiments with this system, as described herein, reveal that long collagen fibers facilitated multi-cellular collective cell streaming, which surprisingly is more robust on the softer substrate. These findings suggest that grouped cells can exploit long fiber architectures to undergo invasion-like streaming through a delicate balance of cell-cell adhesions and mechanoactivation even in soft environments that are otherwise known to restrict cell migration and thus considered benign for cell invasion.

Results

Chemically Modified Polyacrylamide Hydrogel Promotes Collagen Tethering with Tunable Collagen Fiber Length.

The approach disclosed herein for intermediate linker-free ECM protein conjugation to the PA gels, applies a whole gel modification technique through creating active sites in the polymeric network of PA by co-polymerizing N-Ethanal acrylamide (EA) with acrylamide and bis-acrylamide as shown in FIG. 1. EA is an oxidized product of N-Hydroxyethyl acrylamide (HEA), which was oxidized using an oxidizing agent, Pyridinium chlorochromate (PCC) to generate primary aldehyde groups in HEA molecules. PCC, also known as Corey-Suggs reagent, used at room temperature can oxidize primary alcohols into aldehydes in good yields. Free aldehyde groups were generated in the oxidized product named EA bind to the N-termini (ε-amino groups) of collagen by forming strong carbon-nitrogen double bond, which is known as Schiff's base bond (see e.g., FIG. 1A). This ECM protein binding does not require any intermediate crosslinker, such as sulfosuccinimidyl 6-[4'-azido-2'-nitrophenylamino] hexanoate (sulfo-SANPAH) or N-Hydroxysuccinimide (NHS)-ethyl (dimethylaminopropyl) carbodiimide (EDC).

Figures 1B, 1C, 1D:
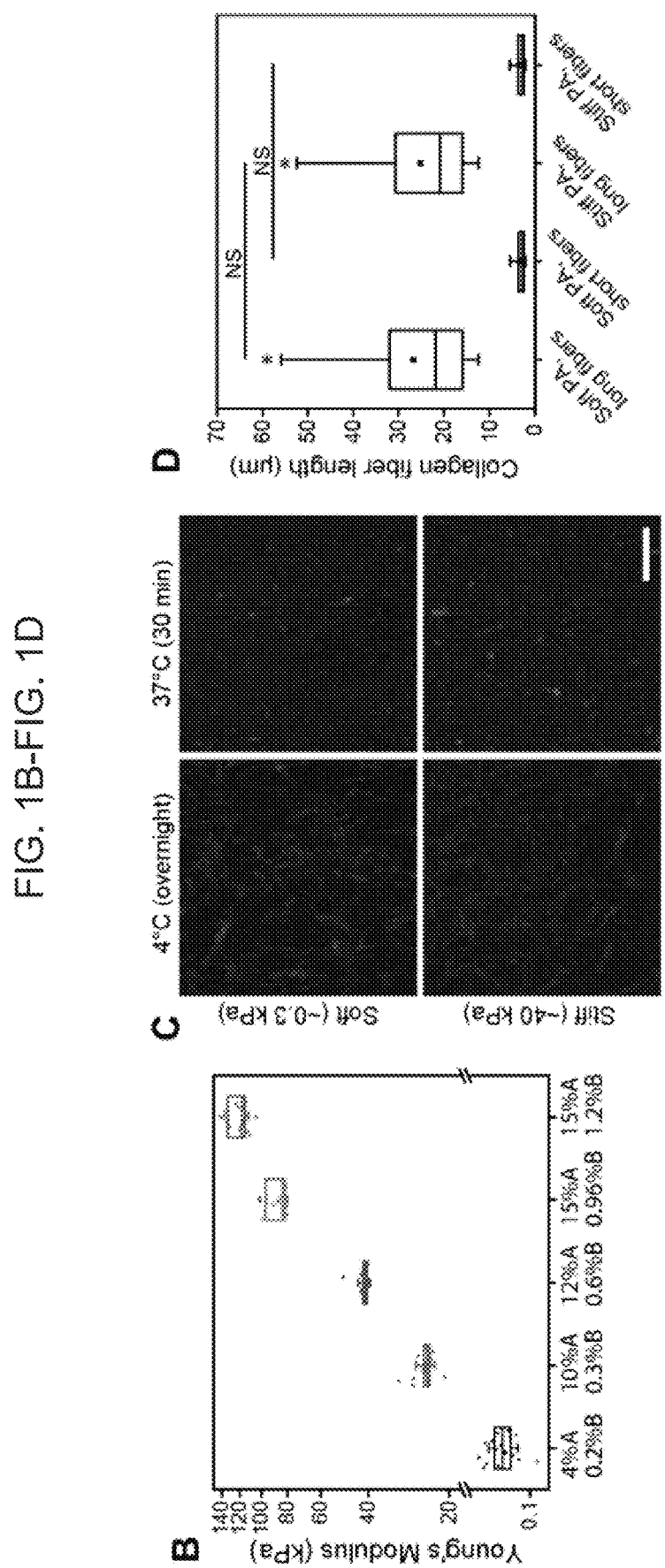
Figure 1E:
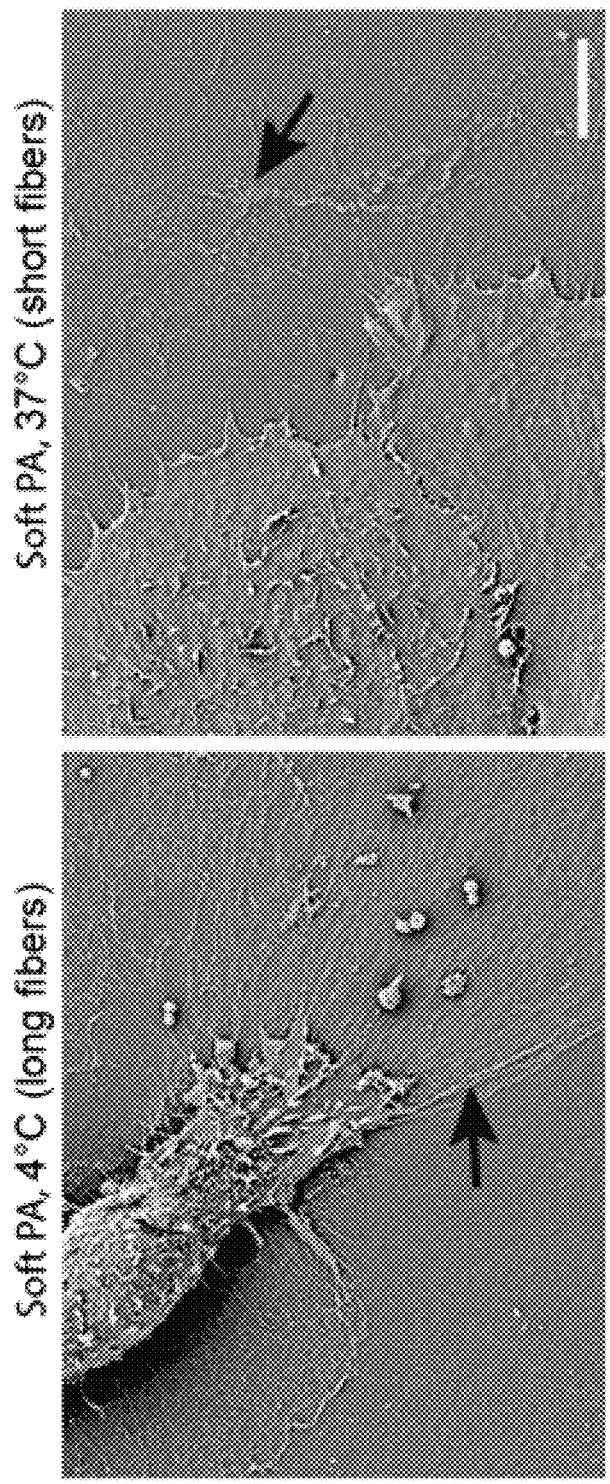

The Young's moduli of the synthesized PA gels of various compositions was measured and the values are reported in FIG. 1B. Because a small amount of oxidized HEA was added into the conventional acrylamide (A)/bis-acrylamide (B) mixture before polymerization and the added EA copolymerized with acrylamide and bis-acrylamide, the bulk stiffness of the modified PA gels did not change significantly. In this study, the compositions, 4% A:0.2% B and 12% A:0.6% B that were used resulted in the Young's Modulus of 0.31±0.03 and 41.5±0.5 kPa, respectively, based on AFM measurements. The fPA gels of the stiffnesses of ~0.3 kPa and ~42 kPa are referred to as 'soft' and 'stiff', respectively.

Figure 8:
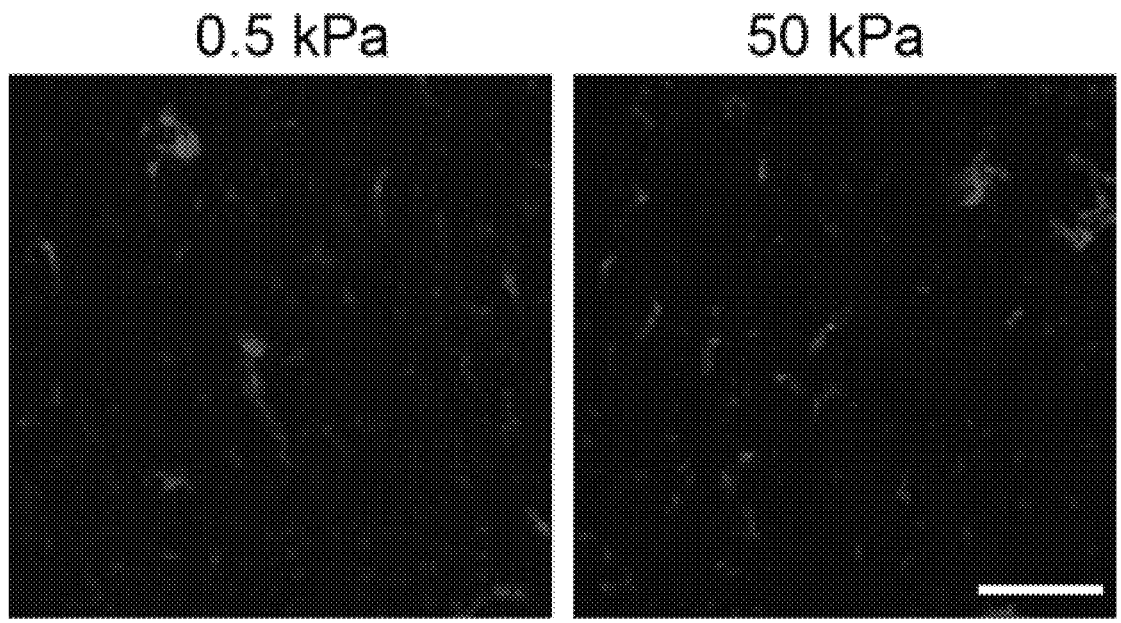
FIG. 8 is a series of images showing non fibrous collagen coating on pristine PA gel. Confocal microscopy images of fluorescently labelled collagen I on soft (0.5 kPa) and stiff (50 kPa) sulfo-SANPAH-treated pristine PA gels, showing non fibrous patchy collagen coating. Scale bar=100 µm.
Figure 10:
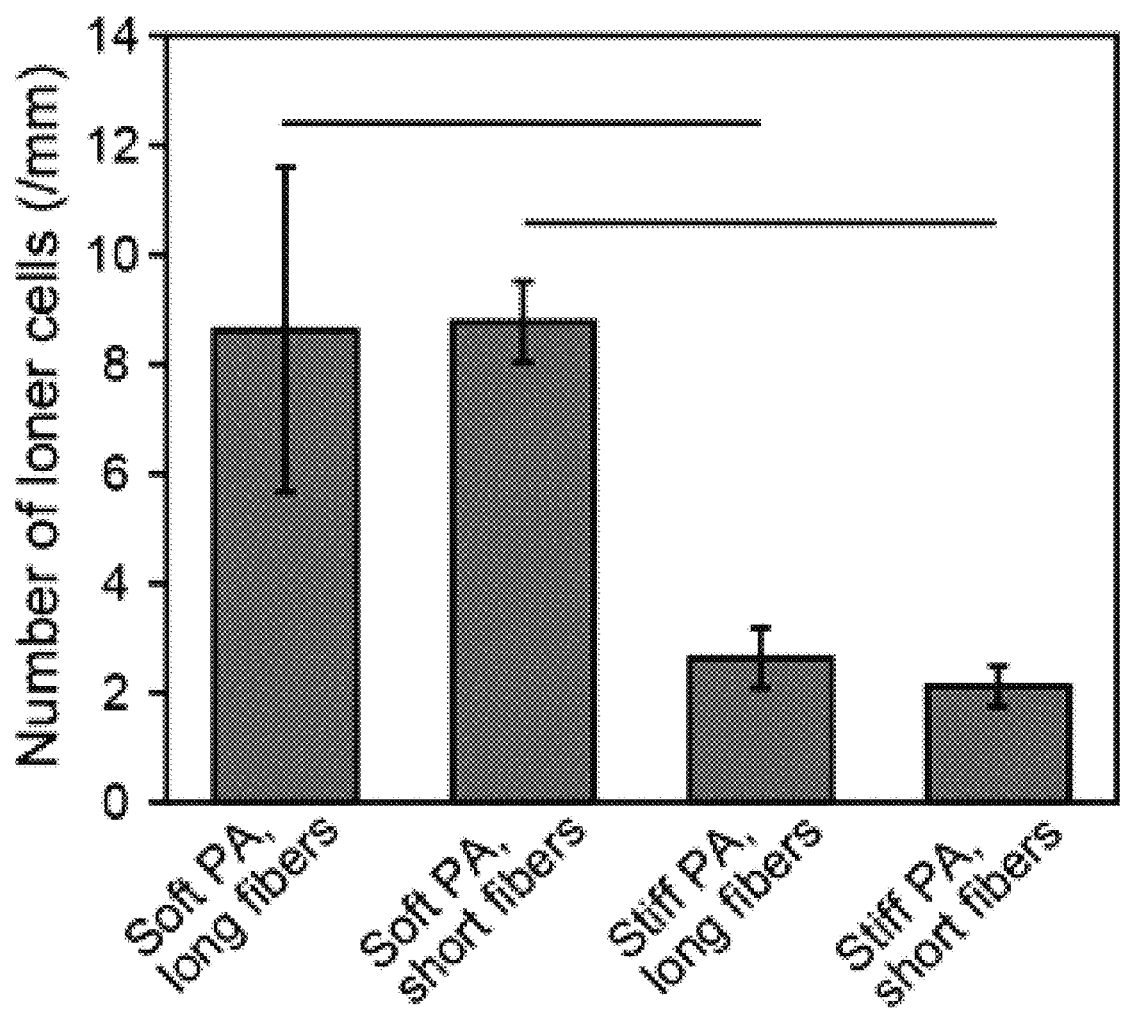
FIG. 10 is a graph showing high number of loner cells on soft gels. Number of loner cells per unit length of the base-line that detached from the epithelial monolayer, showing high number of loner cells on soft gels compared to stiff gels. Lines denote significant difference (p<0.05) in pairwise comparison.
Figure 11:
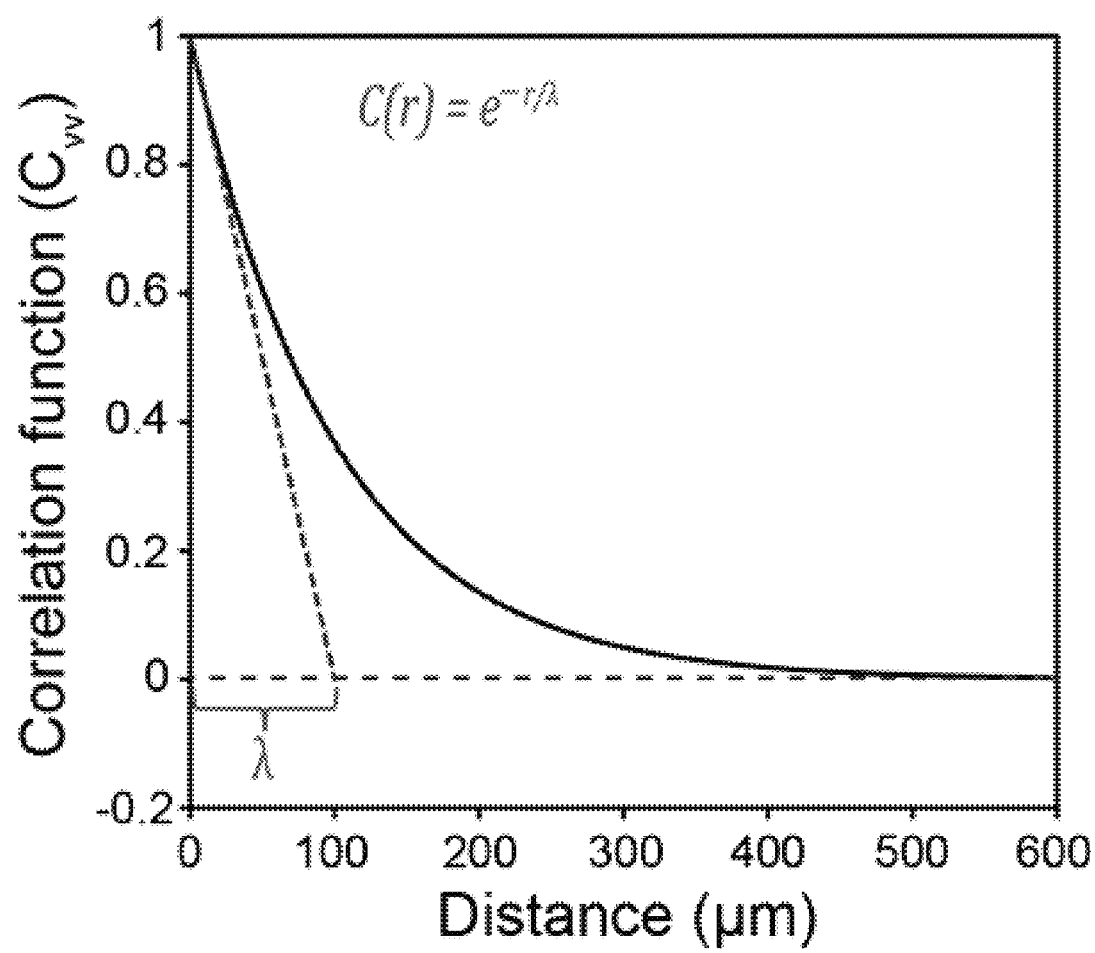
FIG. 11 is a graph showing correlation length calculation. Fitting correlation function (decreasing exponential) is used to obtain correlation length (A).
Figure 12:
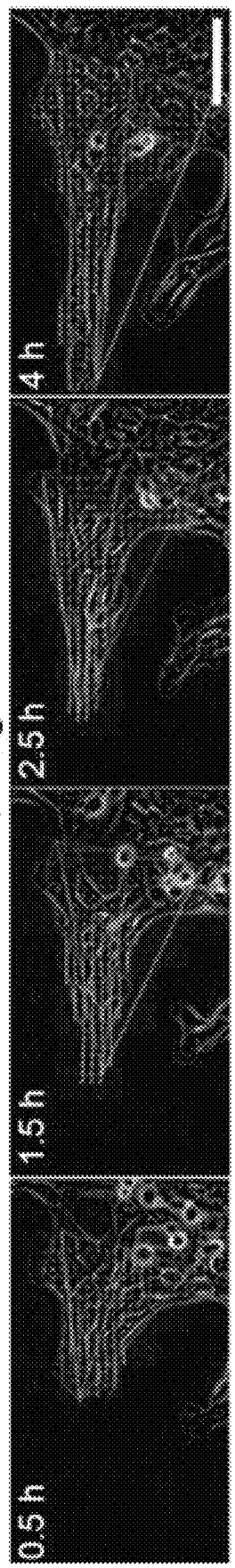
FIG. 12 is a series of images showing computing principle direction of multicellular stream (Vprinciple). Scale bar=100 µm.
Figure 12:
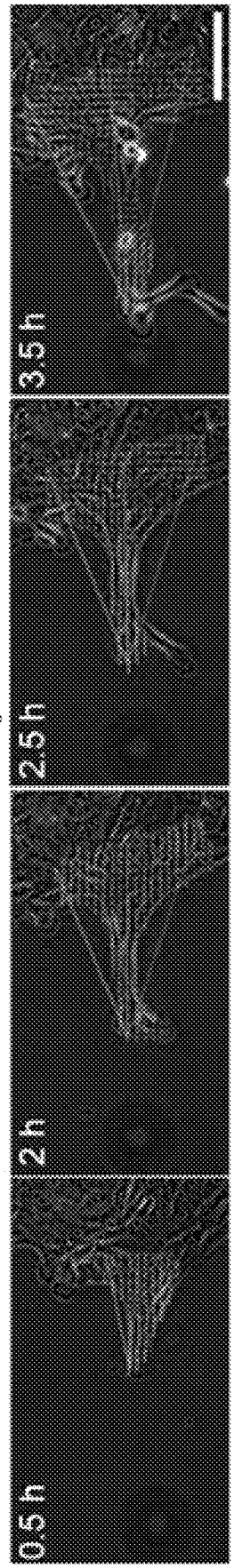

Collagen-I was fluorescently labeled to visualize the conformation of tethered collagen. To tailor collagen fiber structure, the incubation temperature and time was changed during collagen coating on fPA gels as described (see e.g., Materials and Methods). It was observed that short collagen fibers formed on fPA gels of both stiffnesses at 37° C. and shorter incubation time (see e.g., FIG. 10) and long collagen fibers generated at 4° C. and longer incubation time. Whereas, as expected a patchy inhomogeneous collagen coating was observed on sulfo-SANPAH-treated pristine PA gels (see e.g., FIG. 8). Collagen fiber length increased 10 times for the condition at 4° C. compared to the condition at 37° C. (see e.g., FIG. 1D). Importantly, similar collagen structure was achieved on stiff and soft gels in each collagen coating condition. The soft and stiff fPA gels coated with long collagen fibers are referred to as 'Soft PA, long fibers' and 'Stiff PA, long fibers', respectively. The soft and stiff fPA gels-coated with short collagen fibers are referred to as 'Soft PA, short fibers' and 'Stiff PA, short fibers', respectively.

Figure 9:
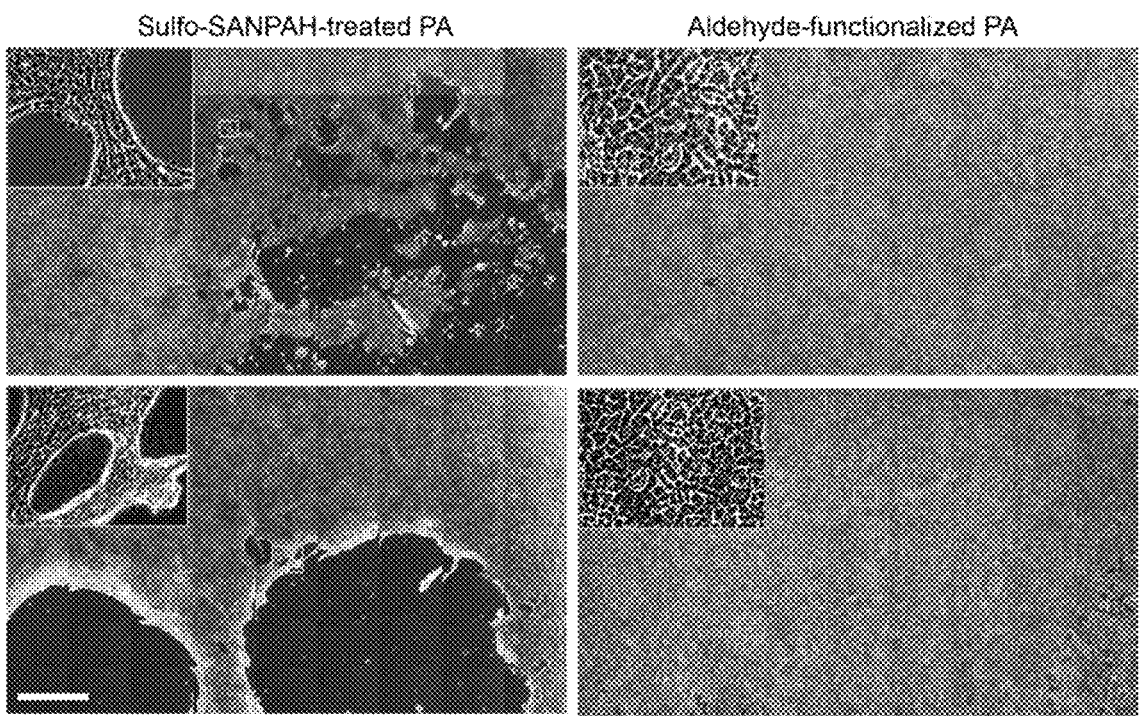
FIG. 9 is a series of images showing fidelity of the aldehyde-functionalized PA gel on epithelial monolayer formation. Phase contrast images of epithelial monolayer on collagen-coated sulfo-SANPAH-treated pristine PA and aldehyde-functionalized PA of very low stiffness (~0.2 kPa). Tiled fields of view are combined that show about 80% of the entire monolayer. Broken or discontinuous cell monolayer is observed on sulfo-SANPAH-treated pristine PA gel. Two different types of discontinuous monolayers on the sulfo-SANPAH-treated gels are shown here. A continuous epithelial cell monolayer was formed on the aldehyde-functionalized PA gel. Scale bar=1 mm.

The fidelity of the pre-functionalized PA gel (fPA) on cell attachment was investigated by comparing with the conventional sulfo-SANPAH-treated PA gel. A mammary epithelial cell (MCF10A) monolayer was seeded on the very soft gels (~0.2 kPa, composition 3% A:0.075% B) of pristine PA and fPA, coated with collagen at 4° C. A significant difference was observed in epithelial monolayer formation, where a broken or discontinuous cell monolayer was observed on sulfo-SANPAH-treated pristine PA gel (see e.g., FIG. 9). A continuous epithelial cell monolayer was formed on the fPA gel.

Moreover, it is important to understand how the long and short collagen fibers on fPA gels regulate the cell morphology. SEM images of the front edge of a migrating MCF10A monolayer show that MCF10A cells on short fibers-coated soft PA are spread and show flat morphology, and collagen fibers (shown with a black arrow) are not remodeled by cells (see e.g., FIG. 1E). But, the cells on Soft PA, long fibers exhibit elongated morphology and collagen fibers (shown with a black arrow) are remodeled and aligned by the cell along its migrating direction.

Multi-Cell Streams Form at the Leading-Edge of Collective Cell Migration on the PA Gels Coated with Longer Collagen Fibers.

The effect of different collagen conformations on the monolayer migration of epithelial cells was investigated by analyzing a small MCF10A cell colony that seeded at the middle of the collagen-coated soft and stiff modified PA gels. Stream-like protruding structures (marked with green arrows, column (i)) were observed at the leading edge of the cell colony on the soft and stiff substrates with long collagen fibers (see e.g., FIG. 2B). However, higher number of fingers with longer length was observed on soft gel compared to the stiff gel (see e.g., FIG. 2C, FIG. 2D). However, the width of the streams on soft and stiff gels exhibited similar width. Therefore, the ratio of length to width of the streams on soft substrates is significantly higher than that on stiff substrates (see e.g., FIG. 2E). On the other hand, no finger-like structure formed at the leading edge of the migrating cell colony on the soft and stiff substrates having short collagen fibers. Though there was no multicellular finger formed on the gels with short fibers, some short but wide protrusions were observed that were called protrusion blebs (marked with orange arrows, see e.g., FIG. 2B, column (ii)). When the ratio of length to average width of multicellular protrusion is equal to or more than 3, it was defined as a protrusion structure stream. When the ratio is less than 3, it was defined as a bleb. Blebs formation is a common phenomenon of epithelial colony migration. But, finger-like protrusion structures generally appear during the cell migration in 3D ECM.

The base-line was defined as the line at the front of the monolayer and behind which there is a continuous cell-monolayer. Because the length of the multicellular fingers is longer on Soft PA, long fibers, the number of cells beyond the base-line is higher than Stiff PA, long fibers (see e.g., FIG. 2F). Moreover, more loner cells were found beyond the base-line on Soft PAs compared to stiff composition (see e.g., FIG. 10). The escaped cells migrated like single cells and migration was not unidirectional. But the migration of the epithelial monolayer was mostly unidirectional and because the migration speed of the cell monolayer is higher compared to the soft gel, the escaped cells were grasped by the monolayer. On the soft and stiff PA gels with short fibers, no fingers were formed and a very limited number of cells escaped from the monolayer and resulted in fewer number of cells beyond the base-line.

Figures 2A, 2B:
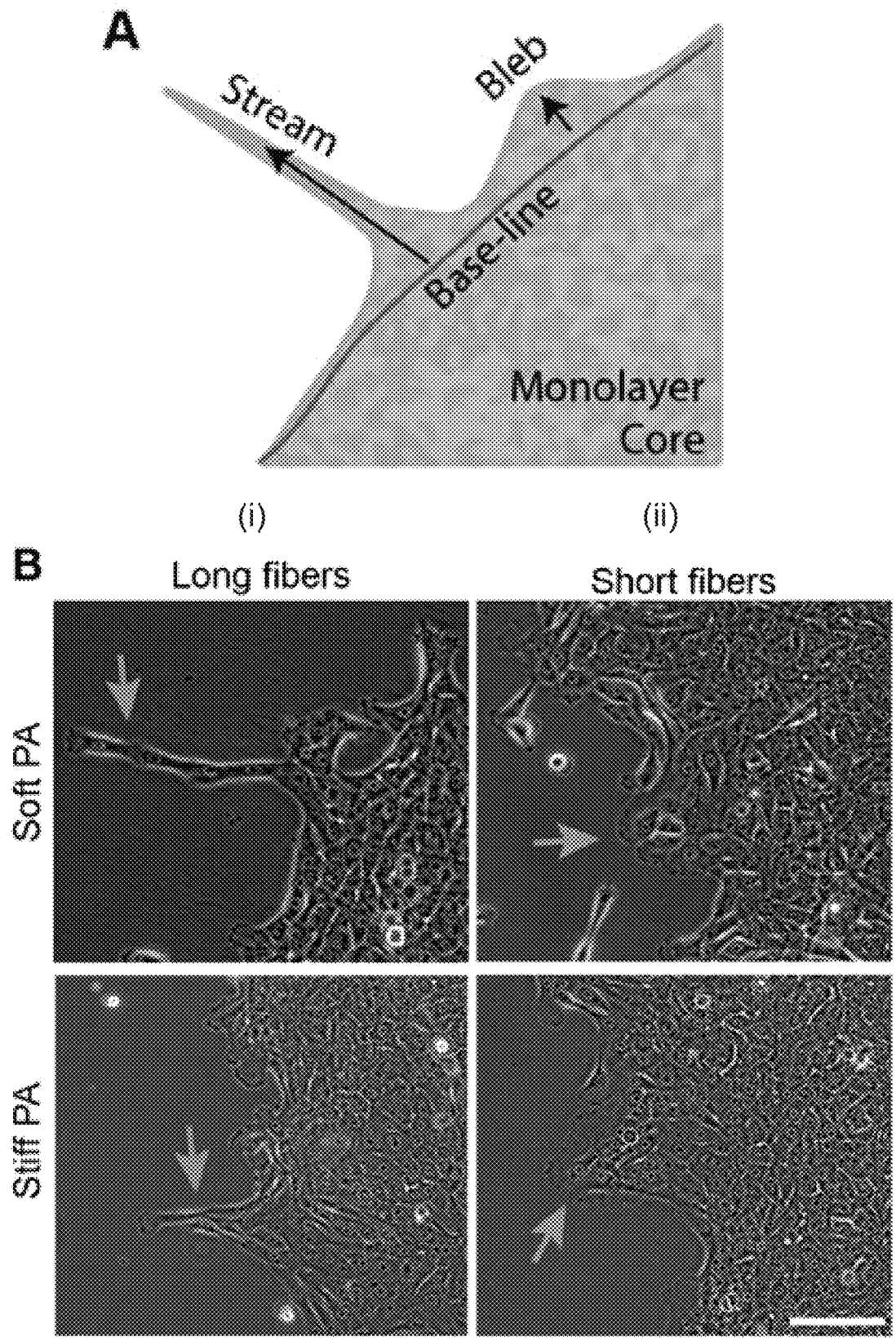
FIG. 2A-FIG. 2H is a series of illustrations, images, and graphs showing finger-like multicellular protrusions are formed at the leading edge of epithelial monolayer on long fibrous collagen-coated gels. (A) A schematic represents different sections of epithelial monolayer that form during MCF10A colony migration on the collagen-coated modified PA gels. (B) Representative images of leading edge of MCF10A monolayer on the four gel systems, where orange arrows and green arrows show the multicellular fingers and protrusion blebs, respectively. Scale bar=200 μm. (C) Average number of multicellular fingers and protrusion blebs per unit length of base-line of the epithelial monolayer. The structures are termed as fingers when the ratio of length to width of multicellular protrusion is equal to or more than 3. (D) Length and width at the base of multicellular protrusions that protruded from the front edge of the epithelial monolayer. (E) Length to width ratio of multi-cellular streams. (F) Average number of cells beyond the base-line of the monolayer per unit length of the base-line. (G) Area and (H) aspect ratio of cells at the three different sections of the epithelial monolayer. Lines denote significant difference (p<0.05) in pairwise comparison. And asterisks represent significant difference (p<0.05) between soft and stiff gels with same fiber dimension and same region of epithelial monolayer.
Figures 2C, 2D, 2E, 2F:
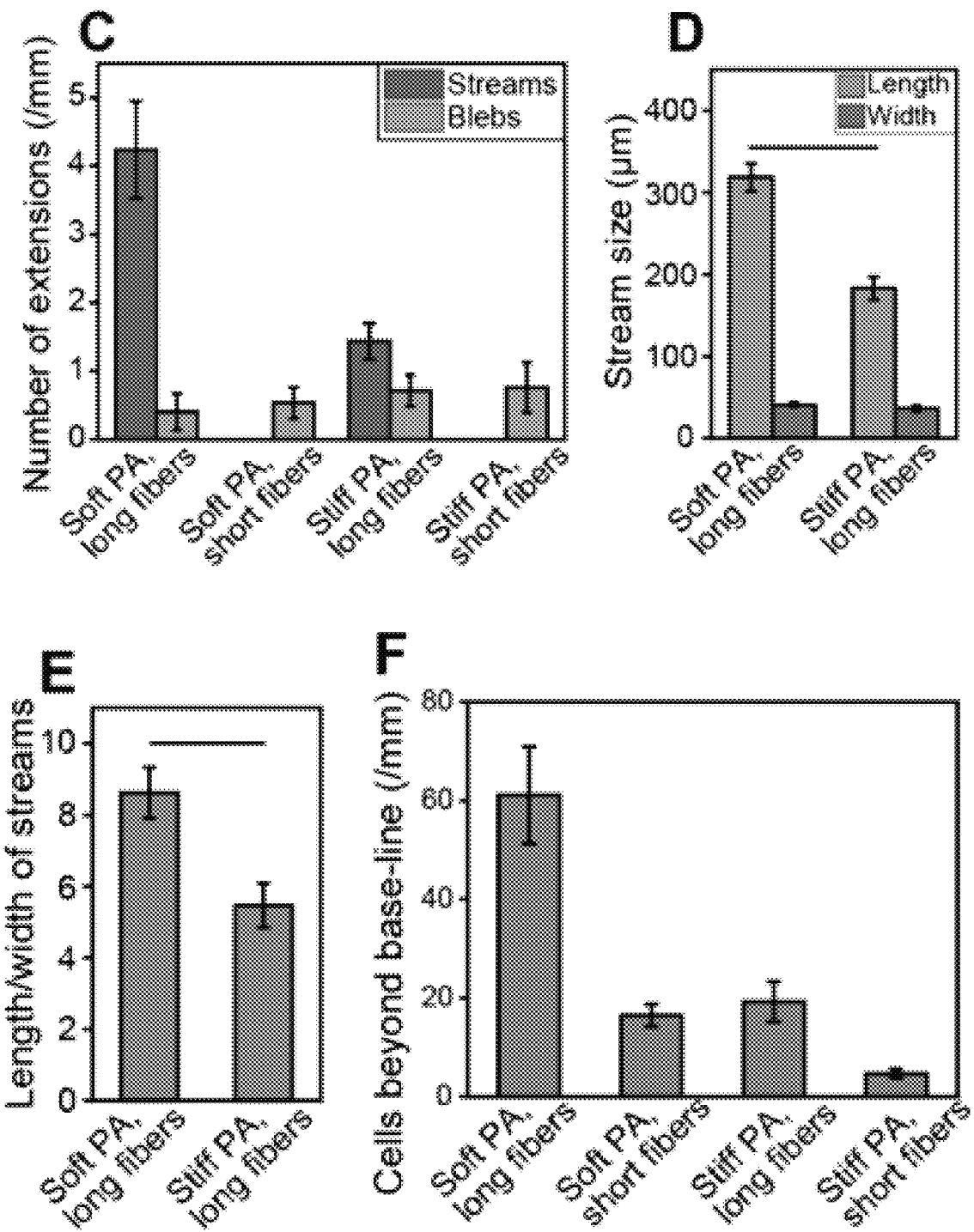
Figure 2G:
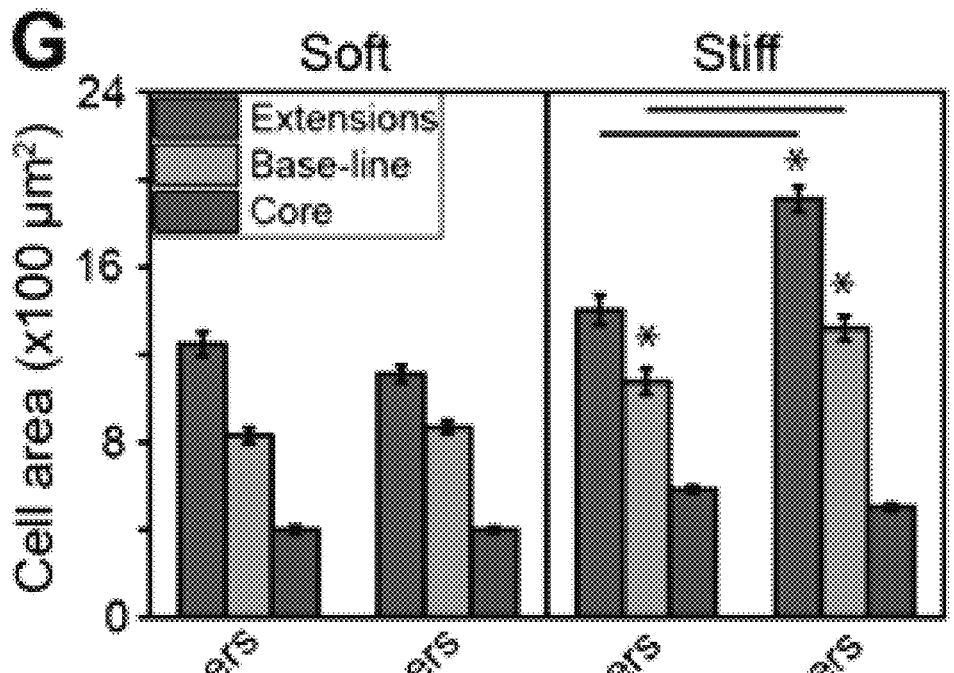
Figure 2H:
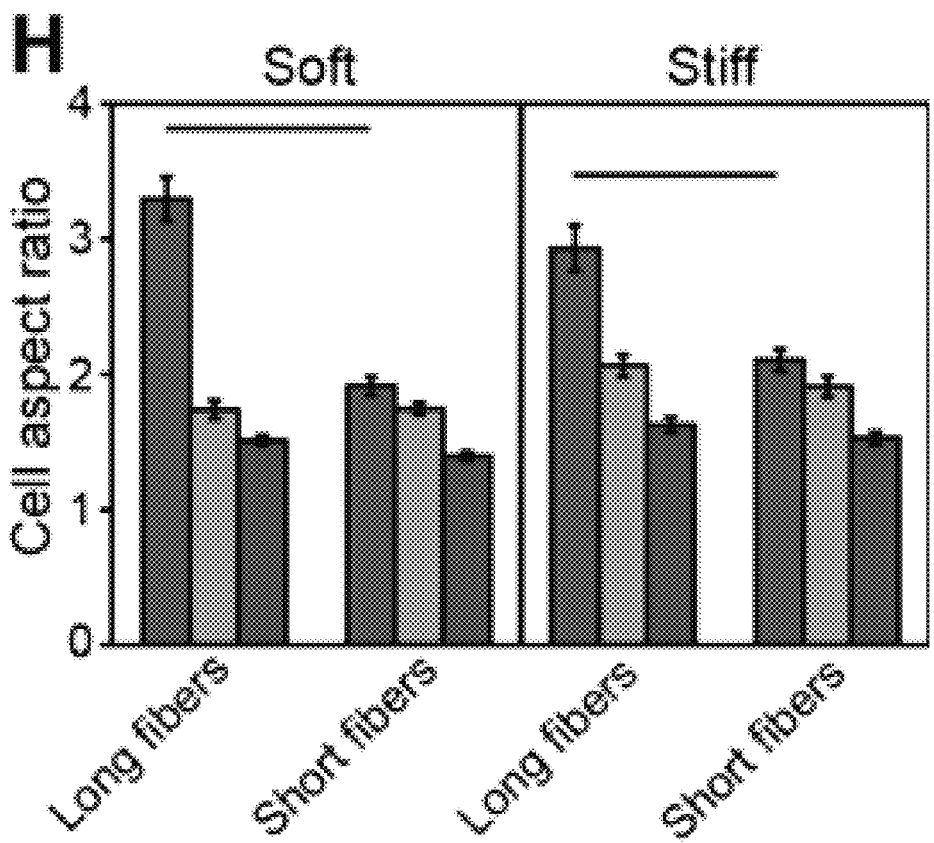

As shown in FIG. 2G and FIG. 2H, cell area and aspect ratio increased from the core of the monolayer to the leading edge, which is a typical phenomenon of an epithelial monolayer. It is interesting to note that though the cell area in the extensions did not change on soft gels due to the stream formation, cells became more elongated in the streams compared to the blebs. Interestingly, on stiff gels, cells in the blebs on the short collagen fibers exhibited high spreading area than the cells in the streams. However, cells in the streams exhibited more elongated morphology than the cells in the blebs.

Longer Collagen Fibers Cause Highest Velocity Gradients on Softer Substrates.

Figure 3A:
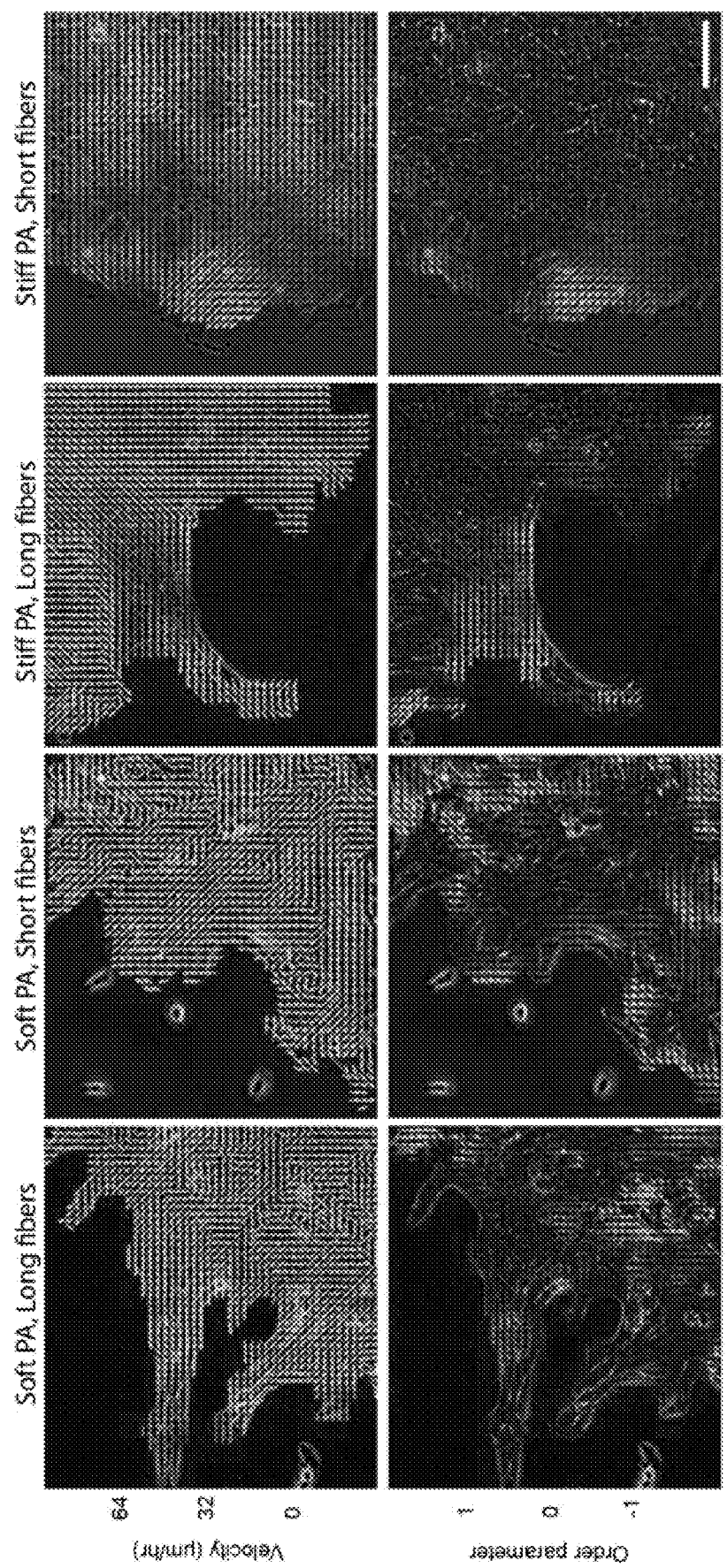
FIG. 3A-FIG. 3E is a series of images and graphs showing finger-like extensions cause higher order parameter and correlation length on soft matrix. (A) Velocity fields (top panel) and order parameter (bottom panel) with color coding of the leading edge of migrating epithelial monolayer on the four types of collagen-coated modified PA gels obtained using PIV. Scale bar=100 μm. (B) Average velocity of the MCF10A monolayer at different regions of the monolayer analyzed by PIV. (C) Average order parameter of the complete front of the monolayer in the field of view. (D) Radial correlation curves for the cells at the extensions and base of epithelial monolayer. (E) Average correlation lengths calculated from the correlation curves. Lines denote significant difference (p<0.05) in pairwise comparison. And asterisks represent significant difference (p<0.05) between soft and stiff gels with same fiber dimension and same region of epithelial monolayer.
Figure 3B:
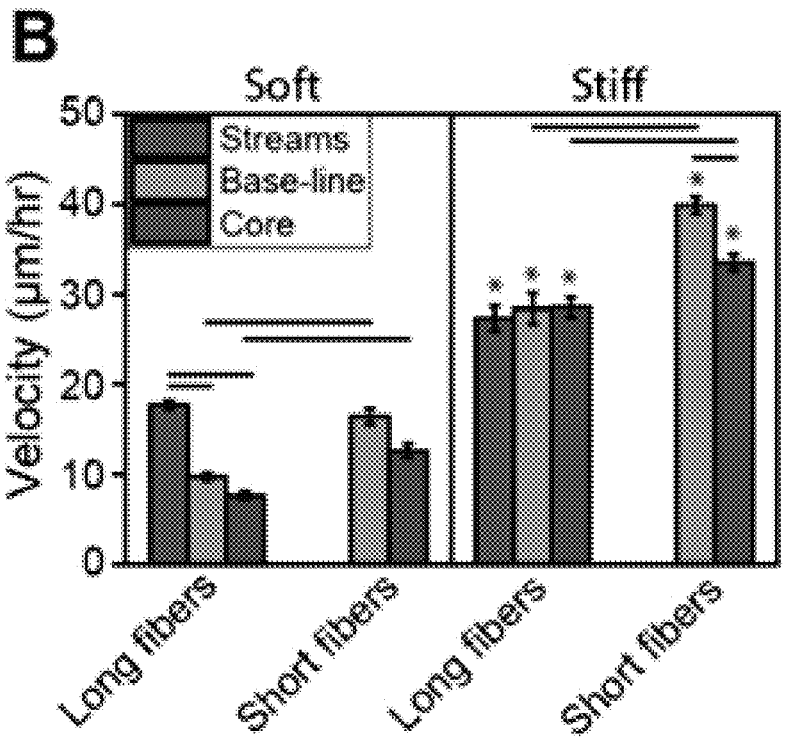

From PIV analysis, it was observed that in soft PA, long fibers, the average cell velocity in the streams is twice the velocity of the cells in the base and core (see e.g., FIG. 3B). This is not true for any other condition. Even in stiff-long substrates where morphology of collective migration is similar to soft-long fibers, i.e. multi-cellular streams formation, no differences were observed between the cell velocities at the finger, base or core of the monolayer. In case of shorter fibers in both soft and stiff fPA, it was observed that migration velocities at the base-line are higher than velocities in the core, but these differences are lesser in magnitude to the differences observed between the fingers and core of soft PA, long fibers.

A similar trend was also observed in the order parameters (see e.g., FIG. 3C) and correlation lengths (see e.g., FIG. 3E) of these two matrices, where both are recorded higher for soft PA, long fibers than soft PA, short fibers. In fact, correlation length in soft fPA gels with long fibers is the highest. Thus higher cell velocity alignment and cell-cell velocity co-ordinations were observed in soft substrates which have long fibers rather than short fibers.

In case of stiff fPA substrates, maximum cell velocity is recorded at the baseline of short fibers rather than the streams and base-line of long fibers. A similar trend is seen in order parameter and correlation lengths, where higher values are seen on short fibers compared to long fibers. Thus in stiff substrates, higher cell velocities, cell velocity alignment and cell-cell velocity correlations are observed in those matrices which have shorter fiber lengths, a trend which is opposite to the one observed in case of soft fPA gels Softer Gels with Long Fibrous Collagen Promote More Sustained Multi-Cell Streaming than their Stiffer Counterparts.

Figure 4A:
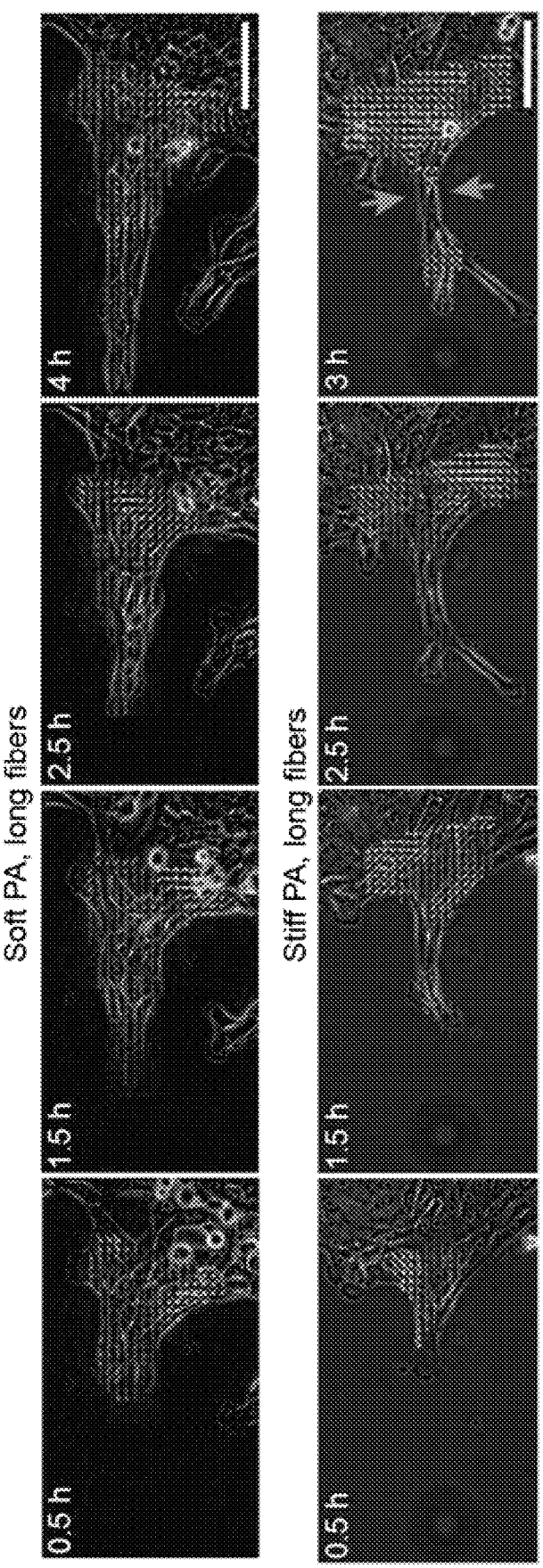
FIG. 4A-FIG. 4C is a series of images and graphs showing highly oriented velocity vectors in the multi-cell streams on soft PA, long fibers. (A) Alignment of the velocity vectors with color coding along the principle direction of the stream. Maximum alignment and dis-alignment (|sin θ|) is indicated by blue and yellow, respectively. Green arrows show the breaking point of the stream. Scale bar=100 μm. (B) Position-time kymographs of velocity components along the principle direction of the stream (v cos θ). (C) Rose-plots of velocity vectors alignment (degrees) along the principle direction of the stream.
Figures 4B, 4C:
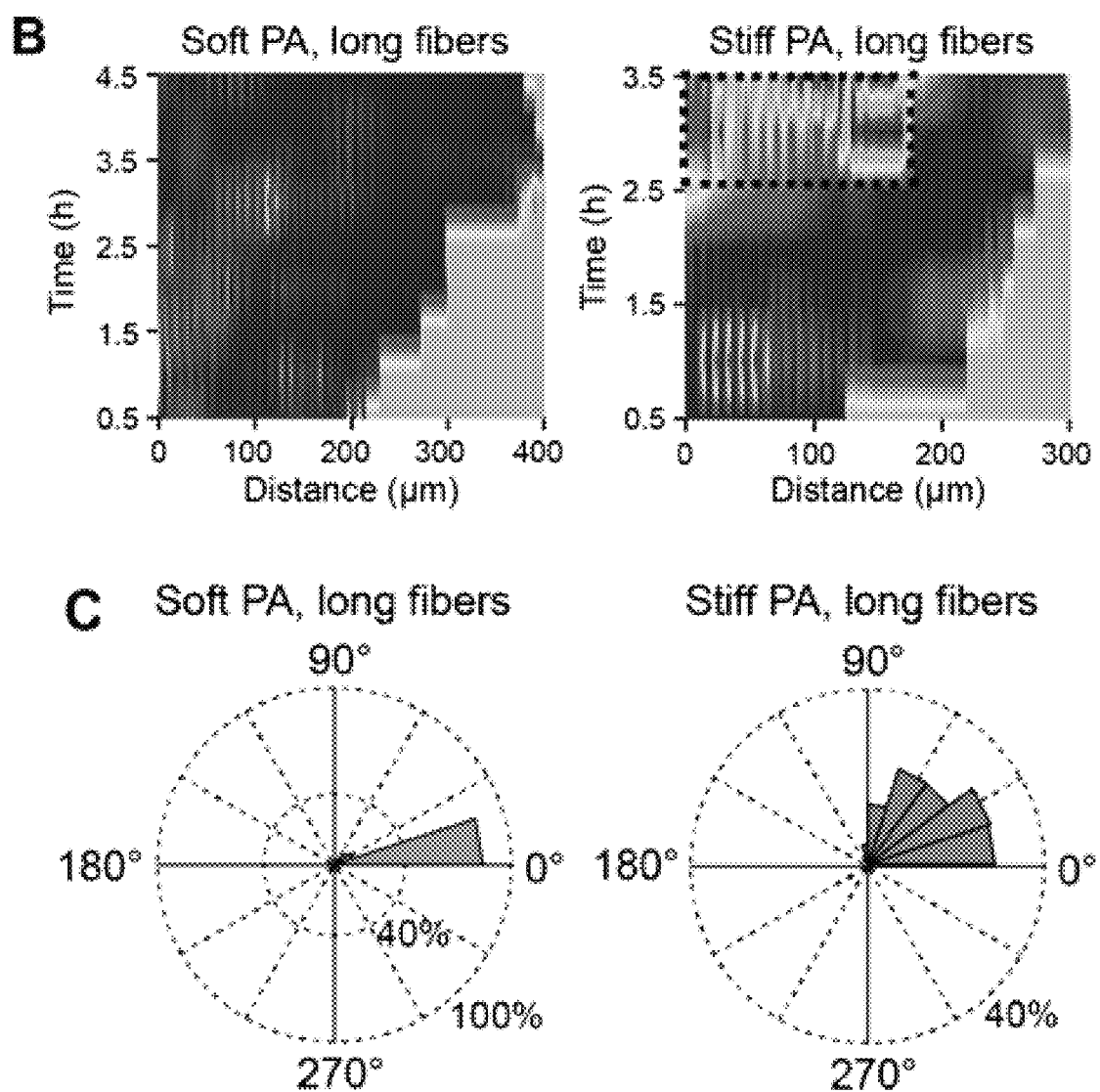

As described earlier and shown in FIG. 2, higher number and longer multi-cellular streams formed on soft PA, long fibers compared to stiff PA, long fibers. Moreover, it was observed that the multi-cellular streams broke frequently on stiff PA, long fibers. Streams formed on softer gels were more sustained than the ones on stiffer gels which resulted in them being longer on softer fPA gels. To understand why more sustained and longer streams formed on softer fPA gels with long fibers, the region of streams and the immediately lagging monolayer was specifically studied for both the conditions—soft fPA with long fiber and stiff fPA with long fiber. FIG. 4A shows the extent of velocity vector dis-alignment ($|\sin \theta|$) with respect to the principle direction of stream (Vprinciple). It was observed that on soft PA gels, velocity vectors stayed aligned along Vprinciple throughout the duration of streaming which is more than 4.5 hours. On the other hand, on stiff fPA with long fibers, gradual dis-alignment in the velocity vectors is observed over time at the base of the stream. After 3.5 hours from the start of streaming, the stream breaks from the base and this coincides with maximum dis-alignment of velocity vectors at the base of the stream. Kymographs for vector alignment along Vprinciple ($\cos \theta$) in FIG. 4B also show that in stiff fPA, 2.5 hr onwards, there is very little velocity vector alignment in the base (dotted region) while in soft fPA gels, vectors are mostly aligned along the entire length of stream throughout the 4.5 hrs. FIG. 4C shows the vector orientation in the final frame in both the conditions. About 90% of the total vectors are oriented between 0° and 18° along the principle direction of the stream on soft gel, proving that the majority of the cells in the stream are highly oriented. On the other hand, vectors in the streams on stiff PA, long fibers are oriented evenly between 0° and 90°, showing low degree of orientation.

Higher Expression of Cellular Mechanosensing Markers in Collective Cell Streaming.

Figure 5A:
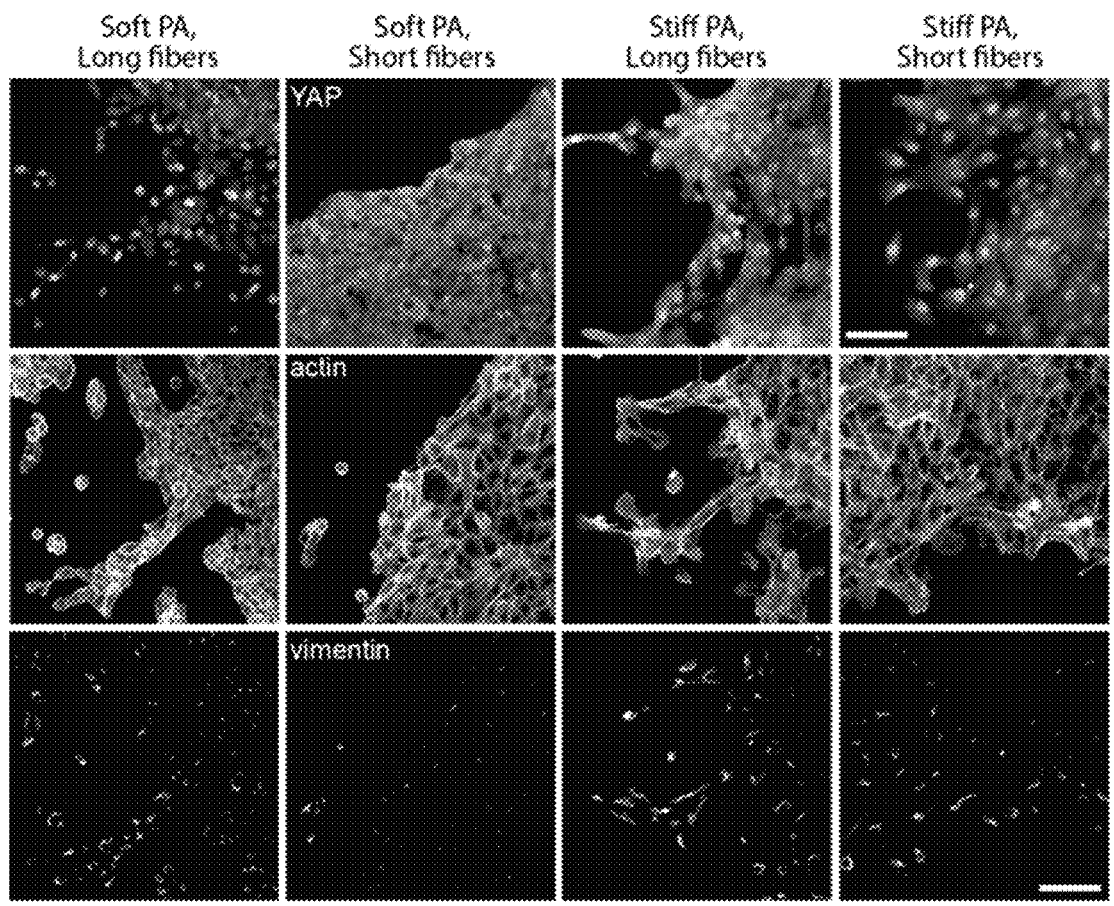
FIG. 5A-FIG. 5D is a series of images and graphs showing high expression of mechanosensing markers in the finger-like epithelial structures. (A) Immunofluorescence images of nucleus and YAP, F-actin and vimentin of MCF10A cells, showing YAP and vimentin expression at the three regions (finger/bleb, base-line and core) of the epithelial monolayer. Scale bar=100 μm. (B) Average nuclear to cytoplasmic ratio of YAP fluorescent intensity of MCF10A and (C) average integrated vimentin fluorescent intensity per cell at the three regions of epithelial monolayer. (D) Average integrated fluorescent intensity of F-actin of MCF10A per unit area of cell in the multicellular fingers or blebs. Lines denote significant difference (p<0.05) in pairwise comparison. And asterisks represent significant difference (p<0.05) between soft and stiff gels with same fiber dimension and same region of epithelial monolayer. Quantifications were carried out by analyzing at least 80 cells each condition for YAP expression, 20 cells each condition for F-actin expression and 10 images each condition for vimentin expression.
Figures 5B, 5C, 5D:
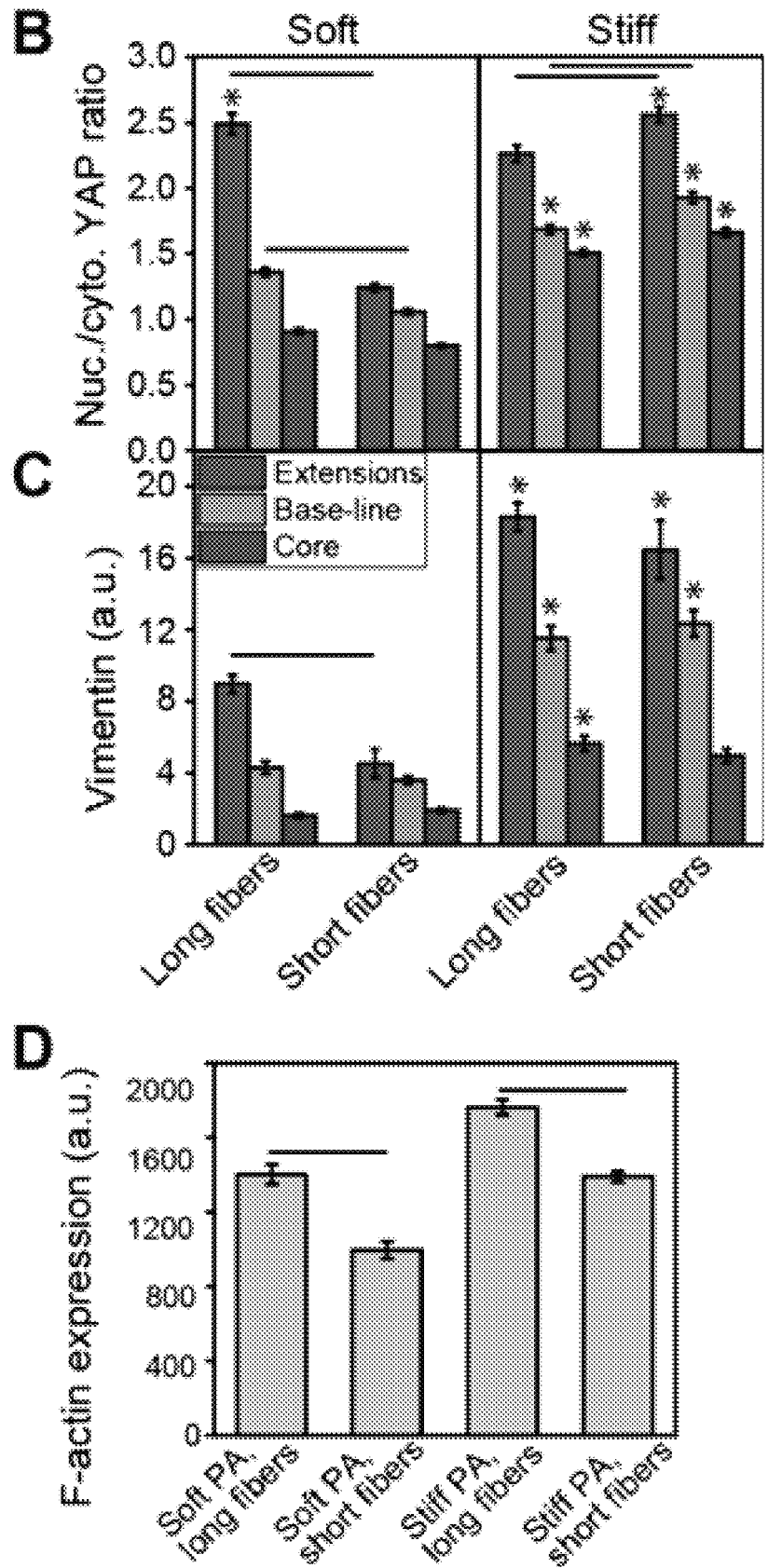

YAP (Yes-associated protein) subcellular localization was analyzed across the three regions (extensions, base-line and core) of the epithelial cell monolayer. As expected, more cytoplasmic YAP expression was observed on soft gels having short and long collagen fibers (see e.g., FIG. 5B). Nuclear to cytoplasmic YAP ratio was found to be increased towards the edge of the monolayer. However, the shifting of the nuclear YAP expression towards the front edge of the monolayer was exponentially higher on the soft PA, long fibers compared to soft PA, short fibers. Very high nuclear YAP localization was found in the streams and the nuclear to cytoplasmic YAP ratio increased to 2.8 times in the streams compared to the core (see e.g., FIG. 5A, FIG. 5B). Interestingly, similar nuclear to cytoplasmic YAP ratio was found in the multicellular fingers or blebs on the stiff gels. Therefore, underlying matrix stiffness-independent nuclear YAP expression was found beyond the base-line on the gel system. At the base-line and in the core of the monolayer, where cell density is higher than beyond the base-line, cell expressed higher nuclear YAP on the stiff gels compared to the cells on soft gels. Therefore, nuclear YAP expression was found to be stiffness-dependent where the cell density was higher.

Similar to the soft gels, a decreasing trend of nuclear YAP was observed from the edge to the core of the monolayer of MCF10A on stiff gels. It was found that cells of high spreading area (see e.g., FIG. 2G) expressed high nuclear YAP. Moreover, cells of high aspect ratio possess high cytoskeletal contractility, which can increase nuclear YAP relocation. Cells were characterized by more F-actin bundles in the streams on long fibrous collagen-containing soft and stiff gels (see e.g., FIG. 5A) compared to the cells on the gels with short fibrous collagen. Moreover, cells in the core of the monolayer were characterized by more cortical F-actin compared to the cells in base-line and fingers/blebs (see e.g., FIG. 5A). Therefore, though the cell area is smaller in fingers, where cells are elongated, high cytoskeletal contractility enhances nuclear YAP localization. Taken together, these data indicate that cell area and cell morphology are important for YAP activity. However, cell area plays a major role over cell morphology on nuclear YAP localization that is corroborated by the outcome of nuclear YAP expression of the cells in the extensions on stiff gels. Cells on stiff PA, short fibers of higher area but lower aspect ratio compared to the cells on stiff PA, long fibers (see e.g., FIG. 2G, FIG. 2H), expressed significantly higher nuclear YAP.

The level of a mesenchymal marker, vimentin, expressed by the cells in the three different regions of the cell monolayer on the soft and stiff gels with short and long collagen fibers was also analyzed. As expected, overall stiffness-dependent vimentin expression was observed in the epithelial cells (see e.g., FIG. 5C). Similar to the YAP expression, increasing trend of vimentin expression was found from the core of the monolayer towards the front edge. Moreover, cells that were beyond the base-line (in streams/blebs) expressed very high level of vimentin. On the soft gels, cells in the streams expressed significantly higher level of vimentin compared to the cells in the blebs (soft PA, short fibers). However, similar vimentin expression was found at the base-line and in the core of cell monolayer on the short and long fibrous collagen-coated soft gels. On stiff gels, a similar trend in increasing vimentin expression from the core to the edge of the monolayer was also observed. Unlike the soft gels, no significant difference was observed between the short and long fibrous collagen-coated stiff PA gels.

Though YAP and vimentin are mechanosensing markers, high nuclear YAP and high levels of vimentin were expressed by the cells in the multi-cellular streams on both stiff and soft gels. In order to understand whether the long fibrous collagen resulted in high cytoskeletal tension, F-actin fluorescent intensity at the front edge of the monolayer on the four gel-systems (see e.g., FIG. 5D) was analyzed. Cells on the soft and stiff gels with long collagen fibers expressed significantly higher F-actin intensity compared to the cells on the gels with short collagen fiber. These outcomes prove that the cells on the long fibrous collagen-coated PA gels experienced high cytoskeletal tension.

Rac1 is necessary for formation of multi-cell streams.

Figure 6A:
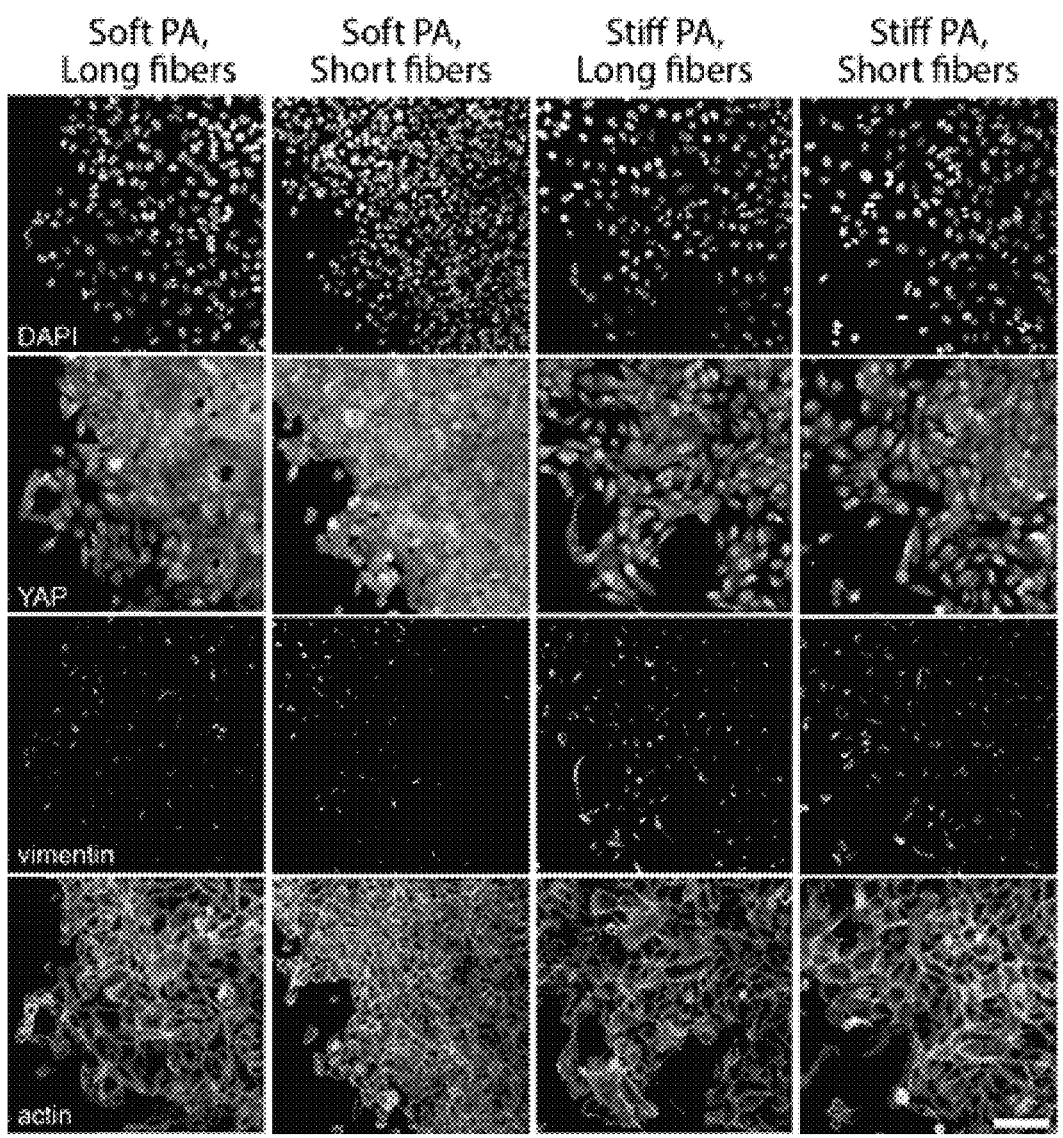
FIG. 6A-FIG. 6E is a series of images and graphs showing Rac1 inhibition restricts multicellular finger formation and cell elongation. (A) Immunofluorescence images of nucleus, YAP, vimentin and F-actin of MCF10A cells treated with Rac1 inhibitory drug. Though no finger is formed, some single cells are escaped from the front edge of monolayer and that are considered as beyond the base-line. Scale bar=100 µm. (B) Average nuclear to cytoplasmic ratio of YAP fluorescent intensity, showing Rac1 inhibition did not alter YAP expression significantly on stiff gels. (C) Average integrated vimentin fluorescent intensity per cell at the three regions of epithelial monolayer, exhibiting Rac1 inhibition decreases vimentin expression of the cells on stiff gels whereas the expression of the cells on soft gels increases. (D) Area and (E) aspect ratio of cells at the three different sections of the epithelial monolayer, showing Rac1 inhibition restrict elongation of cells; however, cell area remains unchanged. Lines denote significant difference (p<0.05) in pairwise comparison. Asterisks represent significant difference (p<0.05) between soft and stiff gels with same fiber dimension and same region of epithelial monolayer. And plus symbols denote significant difference (p<0.05) compared to the wild condition.

Rac1 is a small signaling G protein and member of the Rac subfamily and Rho family of GTPases, which regulates cell-cell adhesions, cell-matrix adhesion, cell migration and cell transformation. Because Rac1 is necessary for formation of lamellipodia, actin-based membrane protrusions and cell-cell adhesion of epithelial cells, a Rac1 inhibitory drug was used to inhibit Rac1 activity of MCF10A cells in order to investigate whether Rac1 is necessary for formation of multi-cell streams on the long fibrous collagen-coated fPA gels. As hypothesized, no stable or consistent finger-like protrusion formed after Rac1 inhibition (see e.g., FIG. 6A). On long fibrous collagen-containing fPA gels of both stiffnesses, more single cells, or cells with minimal cell-cell contact were observed at the front edge of the monolayer.

Upon Rac-inhibition, there is a significant decrease in the cell velocity order parameter values and the correlation lengths in the base region of the monolayer compared to wild type cells. This decrease also coincides with the inability of Rac-inhibited cells at the leading edge to form consistent streams in soft fPA gels with long fibers. In stiff substrates, cell velocities decrease irrespective of the fiber length and the resulting velocities are comparable to that in softer substrates.

The effect of Rac1 inhibition on the expression of mechanosensing markers, YAP and vimentin was also investigated. There was no significant change in nuclear YAP localization in the core of the monolayer compared to the wild type MCF10A (see e.g., FIG. 6B). However, some degree of difference in nuclear YAP localization was found in the extensions and at the base-line, especially for the soft gels. On the soft gels with long fibrous collagen, cells in the extensions exhibited lower nuclear YAP localization compared to the wild type cells, but nuclear YAP expression increased at the base-line. It is interesting to report that the nuclear YAP expressions are not significantly different between the long and short fibrous collagen-coated gels in the individual region of the monolayer except the soft gels at base-line condition. This data reveals that Rac1 inhibition did not alter YAP localization except for the cells in the extensions or at the base-line, where the small degree of changes occurred due to change of cell morphology and change in cytoskeletal contractility. It was observed that cell area and aspect ratio of the cells in the extensions on the soft PA, long fibers dropped significantly (see e.g., FIG. 6D, FIG. 6E). On the stiff PA, long fibers substrate, cells in the extensions exhibited the same area but lower aspect ratio compared to the wild type MCF10A. Combining the two effects could result in a negative outcome in nuclear YAP localization in the cells in the extensions on soft and stiff fPA with long fibers.

Figures 6B, 6C, 6D, 6E:
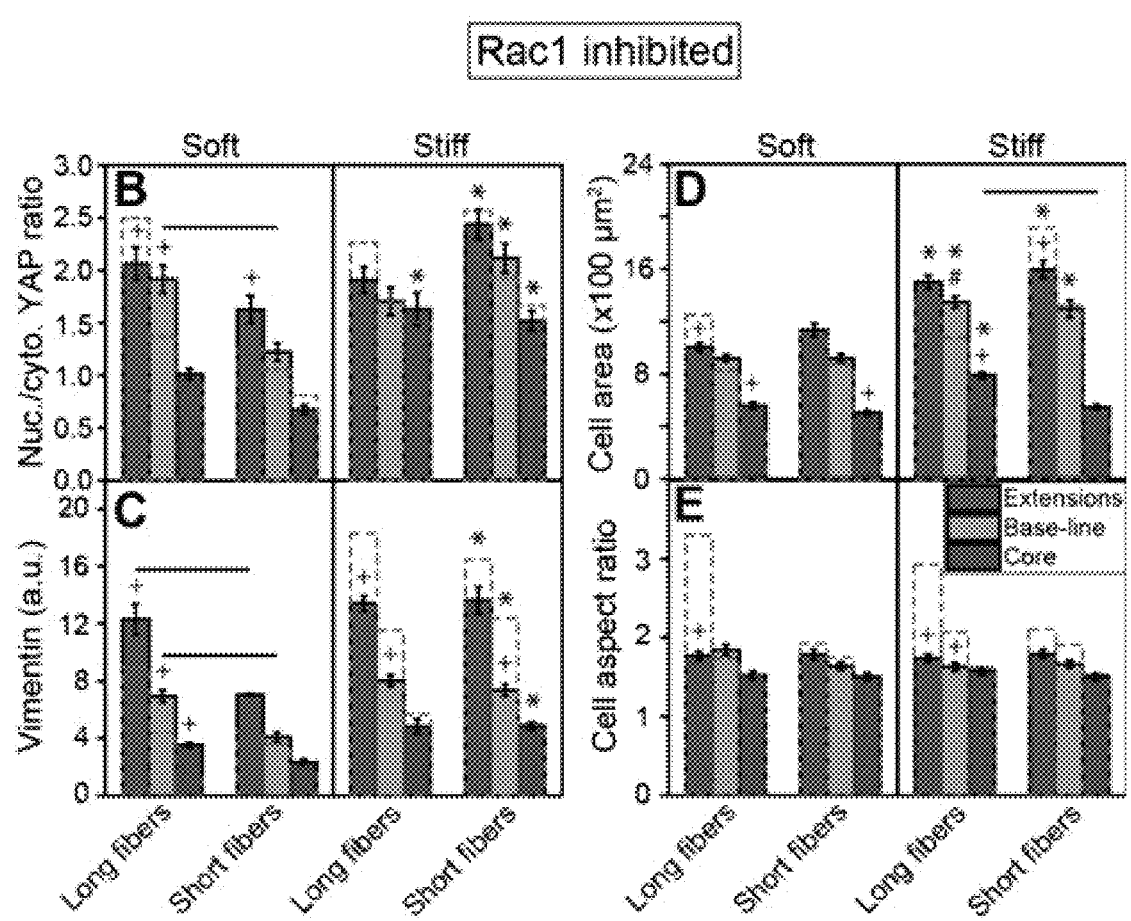
Figure 7A:
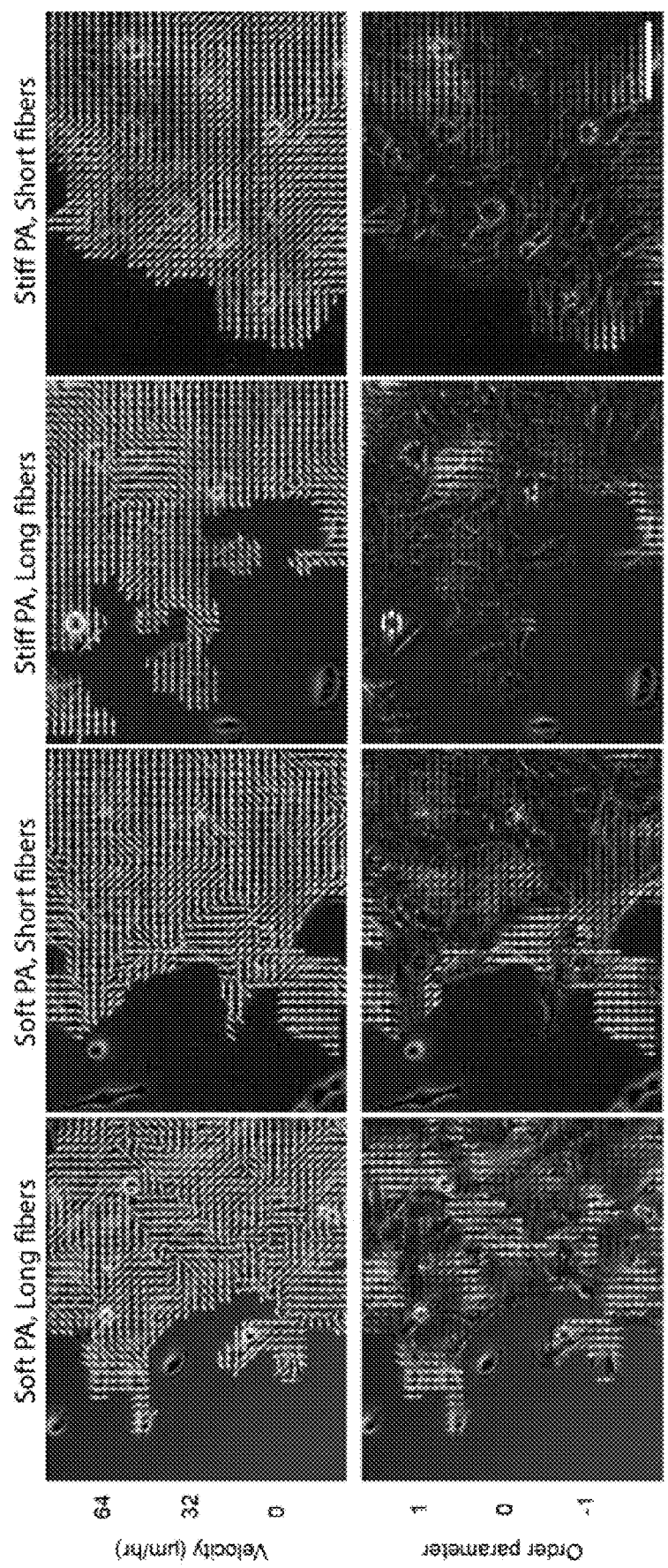
FIG. 7A-FIG. 7E is a series of images and graphs showing Rac1 inhibition diminishes the effect of the stiffness of underlying substrate on the velocity of epithelial monolayer. (A) Velocity fields (top panel) and order parameter (bottom panel) with color coding of Rac1 inhibited epithelial cells on the modified PA gels obtained using PIV. Scale bar=100 µm. (B) Average velocity of the Rac1 inhibited MCF10A monolayer at different regions of the monolayer analyzed by PIV. (C) Average order parameter of the complete front of the Rac1 inhibited epithelial monolayer in the field of view. (D) Radial correlation curves for the cells at the extensions and base of epithelial monolayer. (E) Average correlation lengths calculated from the correlation curves. Lines denote significant difference (p<0.05) in pairwise comparison. Asterisks represent significant difference (p<0.05) between soft and stiff gels with same fiber dimension and same region of epithelial monolayer. And plus symbols denote significant difference (p<0.05) compared to the wild condition.
Figure 7B:
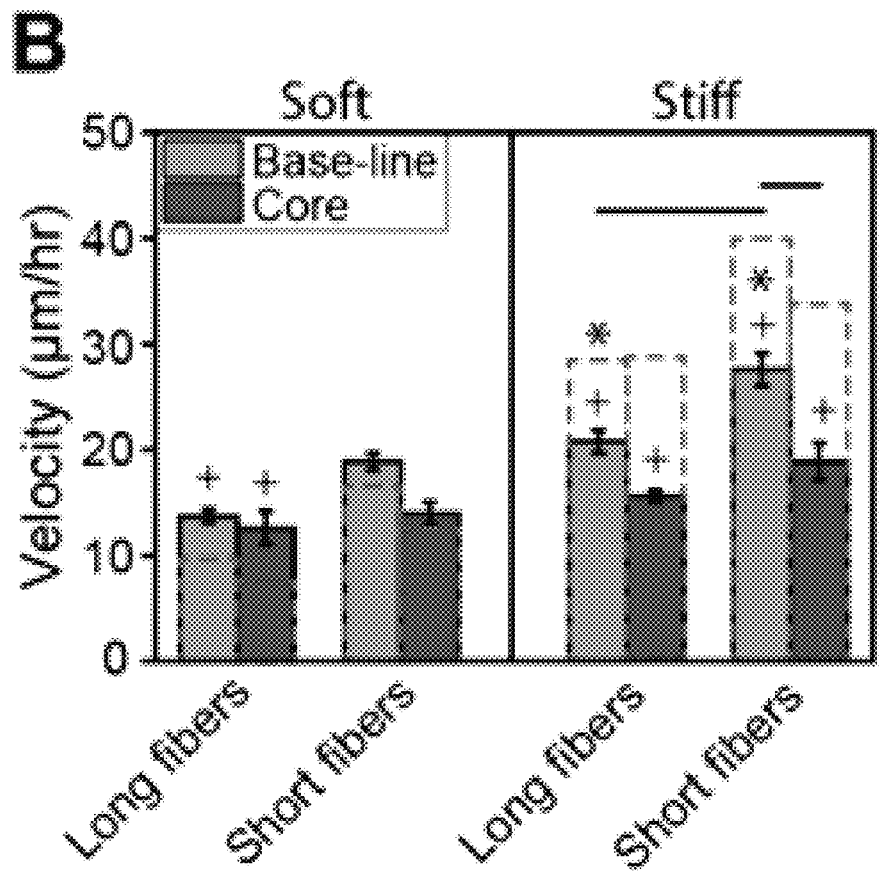
Figure 7C:
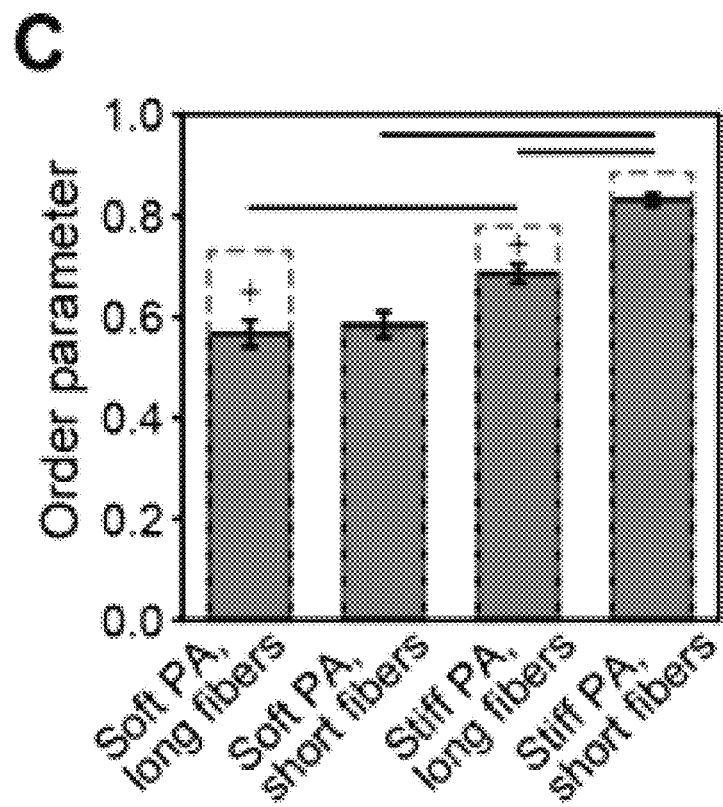
Figure 7D:
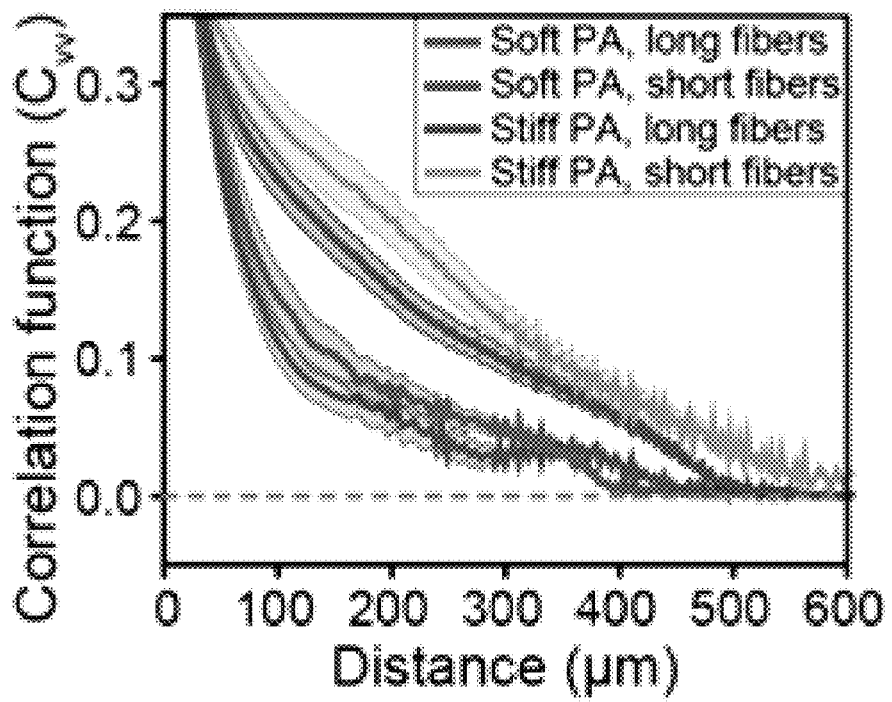
Figure 7E:
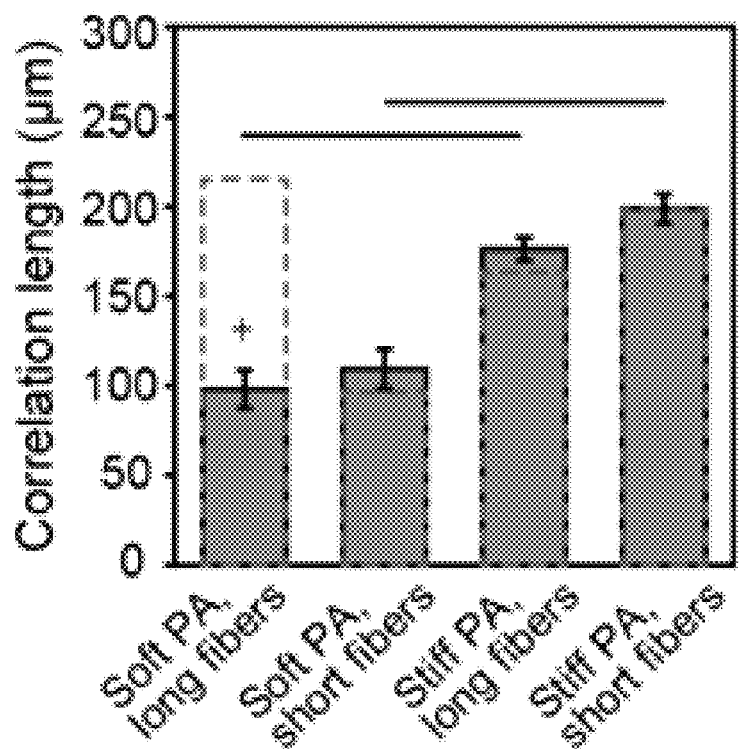

On the other hand, after Rac1 inhibition, vimentin expression was found to be increased in all sections of epithelial monolayer on soft gels, especially on soft PA, long fibers (see e.g., FIG. 6C). This outcome might be attributed to the lack of cell-cell contact due to Rac1 inhibition. But cells on the stiff gels exhibited lower vimentin expression compared to the wild MCF10A especially in the extensions and at the base-line.

Discussion

Cell streaming of collective cell migration generally occurs in 3D ECM, where remodeled collagen fibers guide cells in certain directions. It remains unanswered whether matrix dimensionality or collagen fiber architecture promotes the epithelial cell streaming. Moreover, it is well established that ECM stiffness plays a major role in cell migration. To address this question, the present disclosure describes the development of an aldehyde-functionalized PA gel of tunable stiffness, coated with collagen of tunable fiber dimension that allowed for an epithelial monolayer migration study on a 2D platform. As a result, it was found that long collagen fibers facilitated cell streaming at the front of the monolayer, which was independent from underlying PA stiffness. This outcome may be attributed to the long collagen fibers remodeling by cells that guides the cells along the track. However, more stable multi-cell streams formed on soft PA and persisted for long time. On the other hand, unstable multi-cell streams formed on stiff gel. This result can be attributed to the higher correlated migration on soft PA, long fibers compared to stiff PA, long fibers. All velocity vectors in the multi-cellular stream are oriented in the direction of entire stream on soft gels that facilitate more cohesive streaming. On stiff PA, long fibers velocity vectors in the stream are oriented in different directions, especially at the base of the stream that leads to an unstable structure.

Because different cell monolayer migration phenomena were observed on the PA gels with the same stiffness but different collagen structures, it raises the question whether the stream-like protrusions upregulate the expression of mechanosensing markers through the actomyosin machinery. Given that YAP is the sensor or mediator of mechanical cues of cellular microenvironment, YAP subcellular localization of the migrating epithelial cell monolayer was analyzed. First of all, it was found that density-dependent YAP expression in the monolayer changes as nuclear YAP localization increased towards the leading edge from the core of the monolayer. Similar behavior has been previously reported, illustrating how cell density and cell-cell contact regulate YAP activity through the Hippo pathway. Hippo pathway is active in the middle of the monolayer where cell density is higher, leading to nuclear YAP exclusion and YAP accumulates in the nuclei at the edge of the monolayer where cell density is low. Density-dependent nuclear YAP/TAZ localization has also been previously reported, where human mammary epithelial cells were plated at different densities. Preferential nuclear YAP/TAZ localization was observed at the lowest plating density where cells exhibited no or minimal cell-cell contact. Even distribution of YAP/TAZ in nucleus and cytoplasm was found in the confluent monolayer, whereas, more cytoplasmic YAP/TAZ expression was found in the densely packed monolayer. It was also revealed that aside from the cell density and cell-cell contact, the main determinant factor for YAP/TAZ distribution is actually cell area. Cells attaching to a small surface area have low integrin-mediated focal adhesions, less actin stress fibers, and reduced cell contractility compared to the cells attached to a large surface on the matrix with same stiffness. These mechanical cues are very important for nuclear YAP localization and the cues can be downregulated significantly by lowering only cell area and that can result in nuclear YAP exclusion even on very stiff substrate, e.g. glass. In the present study, it was shown that nuclear YAP expression is related to the cell area. Cell area was found to be increased from the core to the edge of the monolayer, and cells in the streams and blebs have larger area. Simply it can be stated that where the cell density is low, cells get larger. As expected, cells in smaller size were found on soft gels than stiff gels and cells on soft gels expressed lower nuclear YAP than the cells on stiff gels. However, one exception was found for the cells in streams on soft gels, where cells with smaller spread area expressed higher nuclear YAP than the cells in streams on stiff gels. This might be due to the cell elongation in the multi-cell streams, in which cells on soft gels exhibited higher aspect ratio than the cells on stiff gels, leading to higher nuclear stretching and more nuclear YAP transport.

Velocity profiles through PIV analysis explain why cell aspect ratios in multi-cell streams of soft PA, long fibers are higher than those in streams of stiff PA, long fibers. Cell velocities in the fingers are higher than the core of soft PA, long fibers (see e.g., FIG. 3B). This is not so in the case of stiff PA, long fibers, where similar velocities were observed in the all regions of monolayer. This suggests that the relative cell velocity in streams with respect to core is significantly higher in soft PA, long fibers than that in stiff PA, long fibers. This in-turn would lead to higher cell stretching in streams of soft PA, long fibers compared to streams of stiff PA, long fibers thereby increasing their aspect ratios (see e.g., FIG. 2H).

Figure 3C:
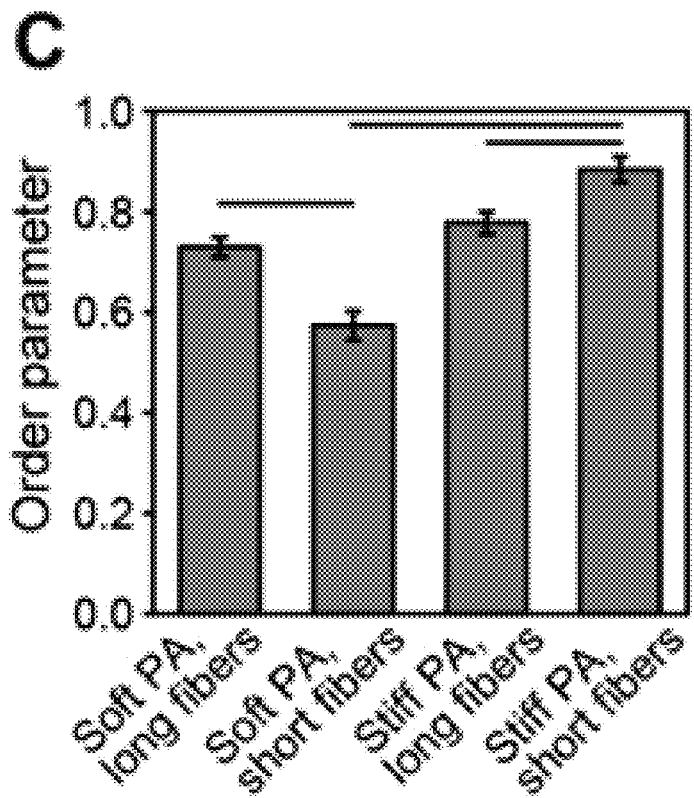
Figure 3D:
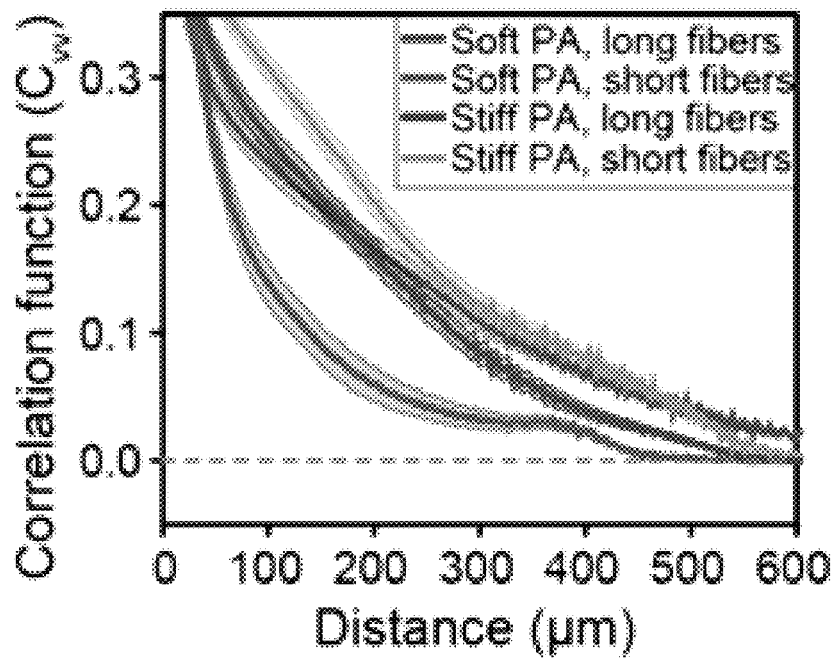
Figure 3E:
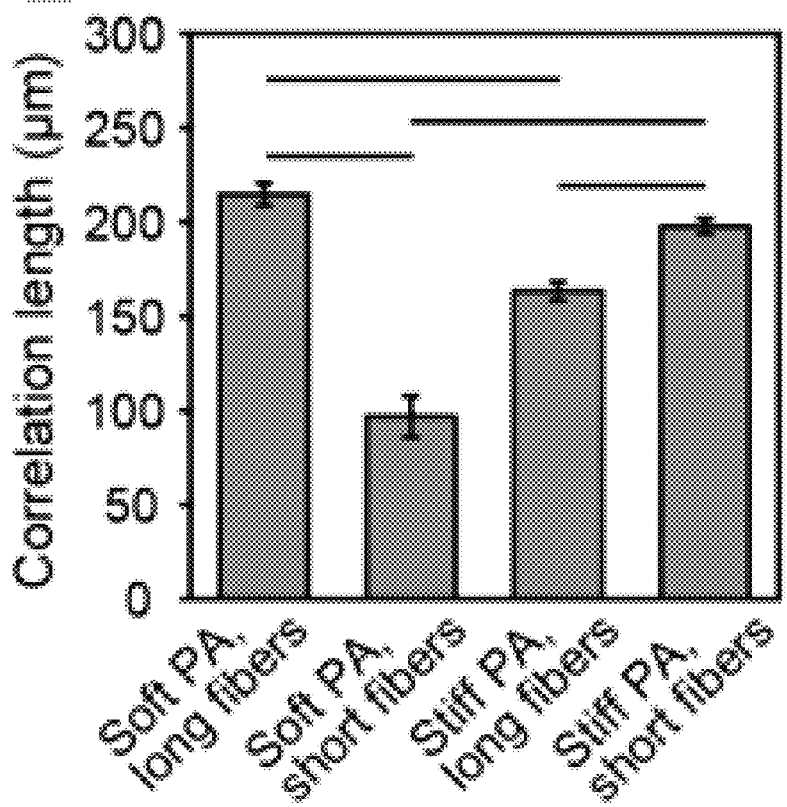

Previously, numerical simulations have shown that finger formation at the epithelial monolayer front can cause more coherent migration of the follower cells in the monolayer, thereby increasing the velocity correlation lengths. In FIG. 3C and FIG. 3D, affirmation to the above theory is observed, where at the migrating front, cells on soft PA, long fibers show higher order parameter and higher velocity correlation lengths compared to those in soft PA, short fibers. It has also been demonstrated that there exists a strong correlation between monolayer velocities and velocity correlation lengths of collectively migrating cells. For epithelial cells which are characterized by strong cell-cell adhesions, the monolayer velocity is directly proportional to the velocity correlation length.

Thus, these findings suggest that in soft matrices, long fibers promote finger formations in the monolayer front which in turn leads to higher velocity correlations at the monolayer front leading to an increase in the velocities. However, this trend is not repeatable in stiff matrices where, higher cell velocities and higher velocity correlations are observed in short fibers. To explore this anomaly, the factors which affect velocities and velocity correlations in the experimental setup should be considered.

It is known that stiffness increases migration velocities and velocity correlations of collectively migrating cells. This was observed in the present experiments, where, compared to soft PA, short fibers, both, stiff PA, short fibers and stiff PA, long fibers show higher migration speeds and velocity correlations in the base and beyond. Therefore, in stiff PA, long fibers, both high stiffness and finger formation are competing cues which are trying to influence velocity correlations at the monolayer front. It is hypothesized that these two competing factors can send contradicting cues to the cells, thereby confusing their decision making and leading to diminished velocity correlations which in turn affect velocities. Also, this may affect the spreading areas of the cells and YAP dynamics.

After Rac1 inhibition, no stable or consistent finger-like protrusion formed on long fibrous collagen-containing fPA gels of both stiffnesses, which might be happening due to the combination of the negative effect of Rac1 inhibition on cell-cell junction and lack of lamellipodia-based protrusions. Long collagen fibers might guide the cells in a particular direction initially. But due to the lack of Rac1, cells did not able to make persistent protrusions in that particular direction and moreover, the follower cells could not establish strong cell-cell junction with the leader cell. On the other hand, because no finger-like structures formed for wild-type MCF10A on short fibrous collagen-coated gels, minimal loner cells were observed after Rac1 inhibition.

It is already known that Rac1 is necessary for cell-matrix adhesion and actin-based membrane protrusion. In addition to the actin motor protein myosin II (Myo II) and the Rho, it has been shown that Rac is a modulator of actomyosin contractility. Activation of Rac by the guanine nucleotide exchange factor Asef2 enhanced cell contractility. Therefore, the reduced actomyosin contractility due to Rac1 inhibition could reduce vimentin expression. Though focal adhesion kinase (FAK) and adaptor protein p130Cas (Cas) are required for transduction of ECM stiffness into intracellular stiffness, it has been previously shown that the intracellular stiffness is determined by Rho family GTPase-mediated actin polymerization. The protein amellipodin is involved in Rac-dependent intracellular stiffening that transmits Rac signals to the cytoskeleton during cell migration. Therefore, inhibition of Rac1 eventually abrogates mechanotransduction pathway. The outcome of the vimentin expression shows that Rac1 inhibition reduced the effect of underlying substrate stiffness on vimentin signals of epithelial monolayer.

Conclusions

Aldehyde-based functionalization of PA gels facilitated collagen fiber formation of tunable length, independent of substrate stiffness. Invasion-like multi-cellular streams with enhanced mechanoactivation formed on both soft and stiff 2D substrates coated with long collagen fibers. More sustained multi-cellular streaming with longer lengths occurred on soft gels compared to stiff gels. This work shows that the collective cell migration phenotypes can be dramatically altered by the collagen fiber dimension on 2D substrate, even on soft matrices which otherwise suppress collective cell migration speed in the sheet mode. Understanding the role of ECM fiber architecture on stiffness dependent collective cell migration might encourage greater links between morphogenesis and tumor invasion.

Materials and Methods

Oxidation of Alcohol to Aldehyde.

N-Hydroxyethyl acrylamide (HEA) was oxidized using Pyridinium chlorochromate (PCC) to generate primary aldehyde groups in HEA molecules. To perform the oxidation reaction, 30 mL of anhydrous dichloromethane (EMD Millipore, Germany) was taken in 250 mL round-bottom flask, in which 1.15 g of HEA (Sigma-Aldrich, USA) was added. Approximately, 3 equivalents (3.23 g) of solid PCC (Acros organics, USA) were added to the 0.2 M solution of the alcohol in anhydrous dichloromethane. 5 g of Celite® (Fisher scientific, USA) was added to the mixture as a solid support so that the reduced chromium salts could deposit over Celite® solid particles and easily removed by filtration. Moreover, in order to moderate the acidity of PCC, 0.615 g (7.5 mmol) of anhydrous sodium acetate (Fisher scientific, USA) was added and the resulting reaction mixture was stirred at room temperature for 15 h. Then the mixture was filtered and collected organic phase was concentrated in a round-bottom flask, giving a crude aldehyde, N-Ethanal acrylamide (EA).

Synthesis of Aldehyde-Functionalized Polyacrylamide Hydrogels and Collagen Coating.

Polyacrylamide (PA) gels were chemically modified by incorporating synthesized EA to facilitate protein conjugation. Chemically modified PA gels with desired stiffness were fabricated on a glass coverslip (diameter 15 mm, Fisher Scientific). PA precursor solutions were prepared by mixing varying amounts of acrylamide (A, Bio-Rad) and bis-acrylamide (B, Bio-Rad) according to the previous stiffness characterization of PA gels as the monomer (A): crosslinker (B) percentages of 4% A:0.075% B, 4% A:0.2% B, 10% A:0.3% B, 12% A:0.6% B, 15% A:0.96% B and 15% A:1.2% B. EA was added to the PA gel precursor mixtures at a volume ratio of 1:75 (EA:acrylamide). To initiate polymerization, 0.5% ammonium persulfate (APS, Sigma) and 0.05% tetramethylethylenediamine (TEMED, Sigma) were added to the precursor mixtures. 35 µL of gel precursor solution was pipetted onto a hydrophobic glass slide, treated with Sigmacote (Millipore Sigma) and placed a silanized 15 mm glass coverslip onto the droplet. Polymerization was performed in a vacuum chamber for 45 minutes. After polymerization, the coverslip containing PA gels were gently detached. The hydrogels were UV sterilized for 2 h in tissue culture hood prior to functionalize with extracellular protein. 1 mL of 0.05 mg·ml$^{-1}$ type I collagen (rat tail collagen, Santa Cruz Technologies) was added onto the PA surface and incubated either overnight at 4° C. or 30 min at 37° C. To investigate the fidelity of the pre-functionalized (fPA) gels on epithelial monolayer formation on very soft gel, pristine PA gels of the composition, 4% A:0.075% B, were fabricated. Prior to add collagen solution, the pristine PA gels were functionalized with a UV-activated heterobifunctional crosslinker (Sulfo-SANPAH, Pierce, USA; 0.5 mg/mL in 50 mM HEPES, pH 8.5) under UV exposure (365 nm) for 10 min as described elsewhere.

Mechanical Characterization of fPA Gels.

Mechanical characterization of PA gels was performed using an MFP-3D-BIO atomic force microscope (AFM, Asylum Research, Santa Barbara, Calif.). Olympus TR400PB AFM probes with an Au/Cr coated silicon nitride cantilever and pyramidal tip were used. Measurements were acquired by indenting the gels using the AFM probe with spring constants of 20-30 pN/nm, as measured by thermal calibration. Elastic moduli were analyzed from force curves using a modified Hertz model.

Fluorescent Labelling of Collagen and Imaging.

To visualize coated collagen onto polyacrylamide hydrogel, collagen I was fluorescently labeled with a slight modification of a previously described method. Briefly, 1.5 mL of a 3 mg mL$^{-1}$ collagen I solution (pH~7.5) was gelled at 37° C. in a well of a 12-multiwell plate. To maintain the pH of the reaction mixture the collagen gel was incubated with 0.2 M sodium bi-carbonate buffer (pH 9.0, Sigma Aldrich, USA) for 10 min. Then the gel was incubated with 500 µL of Sulfo-Cyanine5 NHS ester dye (Lumiprobe Co. USA) solution (dissolved in DMSO) at room temperature in the dark for 1 h. To quench remaining NHS ester 3 mL of 50 mM TRIS buffer (pH 7.5, Sigma Aldrich, USA) was added to the gel. Then the stained collagen gel was washed 6 times with PBS over 2 hours and 200 mM HCl (Sigma Aldrich, USA) was added to solubilize the collagen gel. The collagen solution was dialyzed against 20 mM acetic acid (Sigma Aldrich, USA) at a ratio of 1:1000 (protein solution:dialysis buffer) with continuous stirring at 4° C. for 4 h using a 10000 MWCO dialysis cassette (Thermo Scientific, USA). To prepare the working collagen solution for coating the PA hydrogels, 4% of the unlabeled collagen I solution (50 μg/mL) was removed and replaced with same amount of fluorescently labelled collagen I solution (50 μg/mL). The collagen-coated PA hydrogels were imaged (see e.g., FIG. 2) using a Zeiss LSM 880 laser-scanning confocal microscope (Carl Zeiss Microscopy, Germany). MATLAB supported CT-FIRE was used to measure collagen fiber length automatically from the confocal images as reported elsewhere.

Cell Colony Seeding and Culture.

After incubation for a certain time and at a certain temperature, collagen solution was aspirated and the gels were washed three times with sterile phosphate buffered saline (PBS). Prior to seeding cells, the surface of the gel was air dried for 30 min to facilitate cell colony seeding. To create a small cell colony, MCF10A cells were seeded onto the middle of the gel by putting a tiny droplet of 5 μL cell suspension contains 50,000 cells. Several microliters of cell culture media was added in the well around the sample in such a way that the added media did not touch the seeded cell suspension in order to prevent drying out the cell suspension. Then the samples were incubated at 37° C. and 5% $CO_2$ for 1 hour 15 mins to let the cells attached to the matrix followed by adding media to the samples. Cells were cultured in DMEM/F12 (Invitrogen) supplemented with 5% (v/v) horse serum (Invitrogen), 20 ng/mL epidermal growth factor (EGF, Miltenyi Biotec Inc), 0.5 mg/mL hydrocortisone (Sigma-Aldrich), 100 ng/mL cholera toxin (Sigma-Aldrich), 10 μg/mL insulin (Sigma-Aldrich), and 1% (v/v) penicillin-streptomycin (Sigma-Aldrich). In order to understand the efficiency of homogenous cell attachment to the surface of the PA gels, multiple phase contrast images (10×) of the epithelial cell monolayer were acquired using a tile function of ZEN program of a Zeiss AxioObserver Z1 microscope covering a wide area (9 mm×5 mm). A single image was generated by stitching the tile images using ImageJ.

To investigate the effect of Rac1 on finger-like protrusion, the Rac GTPase inhibitor NSC23766 (Santa Cruz Biotechnology) was added to the cell culture medium at the final concentration of 20 μM at least 16 h after cell seeding once the cell monolayer formed. After adding the drug, cell monolayer was tracked for the next 24 hours using time-lapse microscope.

Time-Lapse Microscopy.

Phase contrast live cell imaging was performed using a Zeiss AxioObserver Z1 microscope (Carl Zeiss Microscopy) equipped with an incubation chamber for controlled temperature, humidity, and $CO_2$, and a motorized, programmable stage. In each experiment, phase contrast images were acquired every 30 min over a 48 h period using 10× objective. Number of multicellular fingers and protrusion blebs and their dimensions were analyzed for the phase contrast images of the migrating cell monolayer after 36 hours of cell seeding in all conditions. Length and width of the protruding structures were measured manually with ImageJ (National Institutes of Health). Width of the finger was measured at the base of the cell monolayer as shown in FIG. 2A. Number of cells beyond the base-line of the monolayer was also counted manually and presented as the number of cells per unit length of the base-line. Using ImageJ, cells were manually outlined and the cell area and aspect ratio were measured for at least 100 cells per condition. Aspect ratio describes a cell's elongation, and is defined as the ratio of major axis to minor axis of the best-fit ellipse for a cell.

Particle Image Velocimetry (PIV).

PIV analysis was performed to calculate spatiotemporal profiles of velocity magnitudes through PIVlab package in MATLAB. PIV was run up to three passes of 64, 32 and 16 pixel windows to improve sub-pixel resolution. Upon running the package, the two mutually perpendicular velocity components; $u_{i,j}$ and $v_{i,j}$ were obtained. Using these two velocity components, the resultant velocity was calculated at each location. The mean velocity $$\langle \vec{v} \rangle$$

was then calculated and subtracted from the velocity fields $$\vec{v}* = \vec{v} - \langle \vec{v} \rangle.$$

To calculate cell alignment, order parameter was calculated which is defined as cosine of the angle which the velocity vector makes with principle velocity vector. Principle velocity vector is the vector sum of all velocity vectors in a given frame. To calculate the cell-cell coordination, velocity correlation lengths ($E_{vv}$) were calculated. First, autocorrelation function, $C_{vv}$ was computed by averaging the correlation coefficients over all the directions and subsequently time averaged over 2.5 hr-long sliding window, i.e. 5 frames.

$$C_{vv}(\delta r, t) = \left\langle \frac{\langle \vec{v}*(\vec{r}+\delta\vec{r}, t) \cdot \vec{v}*(\vec{v}, t) \rangle_r}{\sqrt[2]{\langle \vec{v}*(\vec{r}+\delta\vec{r}, t)^2 \rangle_r \langle \vec{v}*(\vec{r}, t)^2 \rangle_r}} \right\rangle_t$$

Where, subscripts at the end of brackets denote an average over that variable. $C_{vv}$ was then plotted as a function of r and the correlation length ($E_{vv}$) was defined as the distance (r) at which $C_{vv}$ decayed to zero value.

Immunofluorescence, Confocal Microscopy and Image Analysis.

After 2 days of culturing, cells were fixed with 4% paraformaldehyde in PBS, followed by adding 0.1% Triton-X 100 (Sigma, USA) for permeabilization of cell membrane and blocking with 2% BSA in PBS. Primary antibody labelling was performed in 0.5% BSA in PBS overnight at 4° C. with rabbit monoclonal YAP (Cell Signaling; 1:200 dilution) and rabbit monoclonal vimentin (Cell Signaling; diluted 1:200) in separate experiments. Secondary antibody labelling was performed using the same procedure with Alexa Fluor 488-labeled goat anti-rabbit (Cell Signaling; 1:500 dilution) and Alexa Fluor 647-labeled goat anti-rabbit (Cell Signaling; 1:500 dilution) in separate experiments. Nuclei and F-actin staining was performed with 4',6-diamidino-2-phenylindole (DAPI, Santa Cruz Biotechnology; 1:500 dilution) and Rhodamine phalloidin (Invitrogen; 1:200 dilution), respectively. Confocal microscopy was performed using a Zeiss LSM 880 confocal microscope (Carl Zeiss Microscopy), where z-stacks were acquired at 1 μm interval and combined with the Z-projection tool in ImageJ using the maximum intensity setting. All images were taken using same acquisition parameters including laser power, scan speed, and pixel resolution to ensure accurate quantitative image analysis. For quantification of vimentin expression, the Z-projected vimentin images were analyzed using ImageJ. First the images were converted to 32-bit size and each image was processed by subtracting the background. The expression level of vimentin was computed by measuring integrated fluorescence intensity and normalized by cell number. Cell number was computed by using automatic cell counting tool of ImageJ. Vimentin expression was analyzed from at least 10 field of views from three independent experiments. To quantify the subcellular YAP activity, the mean fluorescence intensity of YAP was measured in the nucleus and the cytoplasm by selecting region of interest (ROI). Nuclear YAP localization was calculated by the ratio of nuclear to cytoplasmic YAP intensity. At least 100 cells were randomly selected from 10 to 15 field of views of three independent experiments for YAP activity analysis. F-actin intensity was analyzed by measuring integrated fluorescence intensity in ROIs after subtracting the background signals. F-actin expression is presented per unit area of ROI.

Scanning Electron Microscopy.

Modified PA gels were made as described above, except that 25 µL of PA gel precursor solution was polymerized in between a hydrophobic glass slide and 12 mm silanized glass coverslip. After collagen coating at the specific conditions as described earlier, the gel substrates were fixed in the mixture of freshly prepared 2.5% glutaraldehyde and 2% paraformaldehyde in 0.1 M cacodylate buffer with 2 mM calcium chloride for overnight at 4° C. The gels were rinsed three times in 0.1 M Cacodylate buffer with 2 mM calcium chloride for 10 min each time. Secondary fixation was performed in 1% osmium tetroxide in 0.1 M Cacodylate buffer for 1 h in dark. Then the gels were rinsed three times in ultrapure water (Direct-Q, Merck Millipore) for 10 min each time and subsequently dehydrated in a graded ethanol series (50, 70, 80, 90, and 99.8 v %). Then the samples were dried with a critical point dryer (Leica EM CPD300) and coated with approximately 10 nm of iridium (Leica, ACE 600) before acquiring images using a high-resolution scanning electron microscope (SEM), Zeiss Merlin FE-SEM.

Statistical Analysis.

Data are presented as the mean±standard error. Statistical significance was computed by one-way analysis of variance (ANOVA). The pairwise comparison of the means was calculated with a Bonferroni's test (post hoc comparison). Differences were considered as statistically significant for p-values <0.05.

What is claimed is:

1. A polyacrylamide (PA) hydrogel substrate comprising an aldehyde-containing acrylamide for protein functionalization, wherein protein functionalization of the PA hydrogel enables protein fiber formation of a tunable protein fiber length.

2. The substrate of claim 1, wherein the aldehyde-containing acrylamide is an N-ethanal acrylamide (EA) monomer of formula I

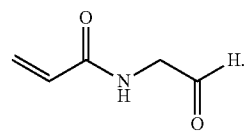

3. The substrate of claim 1, wherein the PA hydrogel further comprises an acrylamide co-polymer and a bis-acrylamide monomer crosslinker.

4. The substrate of claim 1, wherein the PA hydrogel comprises:
   (i) between about 1% and about 20% acrylamide by volume;
   (ii) between about 0.05% and about 5% bis-acrylamide by volume; or
   (iii) between about 0.5% and about 2% N-ethanal acrylamide by volume,
   wherein,
      the PA hydrogel has a Young's modulus or stiffness between about 0.1 kPa and about 200 kPa.

5. The substrate of claim 1, further comprising an extracellular matrix (ECM) protein comprising an N-termini (ε-amino groups) region, bound to an aldehyde group of the aldehyde-containing acrylamide.

6. The substrate of claim 1, wherein the substrate does not comprise an intermediate post hoc crosslinker.

7. The substrate of claim 1, wherein
   (i) the tunable protein fiber length average is between about 0.1 µm and 100 µm; or
   (ii) the substrate is a stiff substrate if a Young's moduli of the substrate is more than about 2 kPa or the substrate is a soft substrate if a Young's moduli of the substrate is less than about 2 kPa,
   wherein,
      the tunable protein fiber length is independent of the substrate stiffness.

* * * * *